US011679075B2

(12) United States Patent
Zucker et al.

(10) Patent No.: US 11,679,075 B2
(45) **Date of Patent: *Jun. 20, 2023**

(54) METHODS FOR ADMINISTRATION AND METHODS FOR TREATING CARDIOVASCULAR DISEASES WITH RESINIFERATOXIN

(71) Applicant: Board of Regents of the University of Nebraska, Lincoln, NE (US)

(72) Inventors: Irving H. Zucker, Omaha, NE (US); Hanjun Wang, Omaha, NE (US)

(73) Assignee: Board of Regents of the University of Nebraska, Lincoln, NE (US)

( * ) Notice: Subject to any disclaimer, the term of this patent is extended or adjusted under 35 U.S.C. 154(b) by 274 days.

This patent is subject to a terminal disclaimer.

(21) Appl. No.: 16/911,070

(22) Filed: Jun. 24, 2020

(65) Prior Publication Data

US 2020/0323771 A1 Oct. 15, 2020

Related U.S. Application Data

(60) Division of application No. 15/668,063, filed on Aug. 3, 2017, now Pat. No. 10,729,643, which is a continuation of application No. 14/484,235, filed on Sep. 11, 2014, now Pat. No. 9,956,166.

(60) Provisional application No. 61/879,440, filed on Sep. 18, 2013.

(51) Int. Cl.
*A61K 31/357* (2006.01)
*A61K 9/00* (2006.01)

(52) U.S. Cl.
CPC .......... *A61K 9/0019* (2013.01); *A61K 9/0085* (2013.01); *A61K 31/357* (2013.01)

(58) Field of Classification Search
None
See application file for complete search history.

(56) References Cited

U.S. PATENT DOCUMENTS

| | | | | |
|---|---|---|---|---|
| 4,920,209 | A | 4/1990 | Davis et al. | |
| 4,939,149 | A | 7/1990 | Blumberg | |
| 5,021,450 | A | 6/1991 | Blumberg | |
| 5,232,684 | A | 8/1993 | Blumberg et al. | |
| 5,962,532 | A | 10/1999 | Campbell et al. | |
| 6,113,915 | A | 9/2000 | Aoki et al. | |
| 6,194,191 | B1 | 2/2001 | Zhang et al. | |
| 8,338,457 | B2 | 12/2012 | Iadarola et al. | |
| 8,829,028 | B2 | 9/2014 | Levy | |
| 8,916,611 | B2 | 12/2014 | Roy et al. | |
| 8,980,223 | B2 | 3/2015 | Jones et al. | |
| 9,289,387 | B2 | 3/2016 | Kottayil et al. | |
| 9,458,093 | B2 | 10/2016 | Duggan | |
| 2002/0058612 | A1* | 5/2002 | Franco | A61K 38/1866 514/8.1 |
| 2004/0146590 | A1 | 7/2004 | Iadarola et al. | |
| 2010/0158973 | A1 | 6/2010 | Weiss et al. | |
| 2010/0290998 | A1 | 11/2010 | Jones et al. | |
| 2011/0086031 | A1 | 4/2011 | Gram et al. | |
| 2015/0051271 | A1 | 2/2015 | Iadarola et al. | |
| 2015/0104439 | A1 | 4/2015 | Roy et al. | |
| 2018/0140544 | A1 | 5/2018 | Zucker et al. | |

FOREIGN PATENT DOCUMENTS

| | | | |
|---|---|---|---|
| WO | 1990014083 | A1 | 11/1990 |
| WO | 1998020867 | A1 | 5/1998 |
| WO | 2000050387 | A1 | 8/2000 |
| WO | 2012045587 | A1 | 4/2012 |
| WO | 2012060845 | A1 | 5/2012 |

OTHER PUBLICATIONS

Caterina, M., et al., "The capsaicin receptor: a heat-activated ion channel in the pain pathway" Nature, Oct. 23, vol. 389, pp. 816-824 (1997).
Eimerl, D. et al., "Epidural Capsaicin Produces Prolonged Segmental Analgesia in the Rat," 97 Exp. Neuro. 169 (1987).
Evans, JA., et al., "Resection of Anginal Pathway for Relief of Anginal Pain," 249 N.E.J. Med. 791 (1953).
Farkas-Szallasi, T. et al., "Vanilloid receptor loss is independent of the messenger plasticity that follows systemic resiniferatoxin administration," Brain Res. 719:213-218 (1996).
Fowler, M.B., et al., "Assessment of the beta-adrenergic receptor pathway in the intact failing human heart," 74 circulation 1290 (1986).
Gao et al. "Cardiac sympathetic afferent stimulation impairs baroreflex control of renal sympathetic nerve activity in rats," Am. J. Physiol. Heart Circ Physiol 286:H1706-H1711 (2004).
Gao et al., "Augmented Input from Cardiac Sympathetic Afferents Inhibits Baroreflex in Rats with Heart Failure," Hypertension, vol. 45, pp. 1173-1181 (2005).
Gorman, A., et al. "Renal nerve responses to cardia receptor stimulation with bradykinin in monkeys," Am. J. Physiol 244:F659-F665 (1983).
International Search Report and Written Opinion for PCT/US2017/027480 dated Jul. 3, 2017, p. 1-12.
Ipe, S. et al. "A comparative study of intrathecal and epidural buprenorphine using combined spinal-epidural technique for caesarean section," Indian J. Anaesth, 2010; 54(3): 205-209, pp. 1-13, 2010.

(Continued)

Primary Examiner — Bong-Sook Baek
(74) *Attorney, Agent, or Firm* — McNeill Baur PLLC

(57) ABSTRACT

There is disclosed a method for administration of a formulation of resiniferatoxin (RTX) to provide cardiac sympathetic afferent denervation when applied in an amount and concentration sufficient to chemically denervate vanilloid 1 receptor (TRPV1)-expressing CSAR (cardiac sympathetic afferent reflex) afferents. There is further disclosed a method for treating heart failure or hypertension and its related indications selected from the group consisting of increased sympatho-excitation, cardiac hypertrophy, increased left ventricular end diastolic pressure (LVEDP), lung edema, and combinations thereof, comprising administering an effective amount of RTX directly to a tissue site selected from the group consisting of epicardium, a T1-T4 dorsal root ganglion and intrathecally to the T1-T4 region of the spinal column.

22 Claims, 20 Drawing Sheets

(56) References Cited

OTHER PUBLICATIONS

Karai, L. et al., "Deletion of vanilloid receptor 1-expressing primary afferent neurons for pain control," The Journal of Clinical Investigation 113(9): 1344-1352 (May 2004).
Karai, L., et al., "Evaluation of Intraganglionic Resinferatoxin (RTX) Injection for Pain Control," Soc. Neuroscience Abstracts (2001).
Lohse, M. et al., "What is the Role of B-Adrenergic Signaling in Heart Failure?," Circ. Res. 93:896-906 (2003).
Longhurst, J. et al., "Cardiac Sympathetic Afferent Activation Provoked by Myocardial Ischemia and Reperfusion," Ann. NY. Acad. Sci. 940:74-95 (2001).
Malliani, A. et al., "Emerging Excitatory Role of Cardiovascular Sympathetic Afferents in Pathophysiological Conditions" Hypertension, 39:63-68 (2002).
Mannes, A. et al., "Resinferatoxin, a potent TRPV1 agonist: Intrathecal administration to treat severe pain associated with advanced cancer—case report," 2010 Annual Meeting Am. Pain Soc., S43, 1 page abstract.
Mitchell, K., et al. "Prolonged analgesic effect of RTX on A-delta type II fibers following peripheral administration," Annual Meeting Am. Pain Soc. S40 (2010).
Nelson, D.A., "Intraspinal steroids: history, efficacy, accidentally, and controvery with review of United States Food and Drug Administration reports," 70 J. Neurol. Neurosurg. Psychiatry 433 (2001).
Olah, Z., et al., "Ligand-induced Dynamic Membrane Changes and Cell Deletion Conferred by Vanilloid Receptor 1", J. Bio. Chem. 276:11021-11030 (2001).
Singh, K. et al., "Adrenergic regulation of myocardial apoptosis," 45 Cardiovasc. Res. 713 (2000).
Szabo, T., et al., "Epidural resiniferatoxin induced prolonged regional analgesia to pain," Brain Research, vol. 840, pp. 92-98 (1999).
Szallasi, A et al., "Effects of systemic resinferatoxin treatment on substance P mRNA in rat dorsal root ganglia and substance P receptor mRNA in the spinal dorsal horn," Brain Res. 815:177-184 (1999).
Szallasi, A. et al., "Resinferatoxin-type phorboid vanilloids display capsaicin-like selectivity at native vanilloid receptors on rat DRG neurons and at the cloned vanilloid receptor VR1," British J. Pharmacology 128, 428-434 (1999).
Szallasi, A., "Duration of desensitization and ultrastructural changes in dorsal root ganglia in rats treated with resiniferatoxin, an ultrapotent capsaicin analog," Brain Research, vol. 503, pp. 68-72 (Nov. 1989).
Szallasi, A., et al., "The Cloned Rat Vanilloid Receptor VR1 Mediates Both R-Type Binding and C-Type Calcium Response in Dorsal Root Ganglion Neurons," Molecular Pharmacology, vol. 56, pp. 581-587 (1999).
Szallasi, A., et al., "Vanilloid receptors: new insights enhance potential as a therapeutic agent," Pain 68:195-208 (1996).
Tominaga, M., et al., "The Cloned Capsaicin Receptor Integrates Multiple Pain-Producing Stimuli," Neuron, vol. 21, pp. 531-543 (Sep. 1998).
Wang, H-J, et al. "Cardiac Sympathetic Afferent Denervation Attenuates Cardiac Remodeling and Improves Cardiovascular Dysfunction in Rats with Heart Failure," Hypertension 64:745-55 (2014).
Wang, W. et al., "Cardiac sympathetic afferent reflex in dogs with congestive heart failure," American Journal of Physiology, R751-R756 (1996).
Wang, W. et al., "Cardiac Sympathetic Afferent Reflexes in Heart Failure," Heart Fail. Rev. 5:57-71 (2000).
Wang, W-Z., et al., "Differential effects of cardiac sympathetic afferent stimulation on neurons in the nucleus tractus solitarius," Nueroscience Letters 409:146-150 (2006).
Wender et al. "The First Synthesis of a Daphnane Diterpene: The Enantiocontrolled Total Synthesis of (+)-Resiniferatoxin" J. Am. Chem. Soc. 119:12976-12977 (Jul. 9, 1997).
Zahner, M., et al., "Cardiac vanilloid receptor 1-expressing afferent nerves and their role in the cardiogenic sympathetic reflex in rats," Journal of Physiology, vol. 551, pp. 515-523 2003.
Zhu et al. "Enhanced Cardiac Sympathetic Afferent Reflex Involved in Sympathetic Overactivity in Renovascular Hypertensive Rats" Exp. Physiol. ;94(7): 785-794 (Jul. 2009).

* cited by examiner

METHODS FOR ADMINISTRATION AND METHODS FOR TREATING CARDIOVASCULAR DISEASES WITH RESINIFERATOXIN

RELATED APPLICATIONS

This application is a divisional of U.S. patent application Ser. No. 15/668,063, filed Aug. 3, 2017, which is a continuation of U.S. patent application Ser. No. 14/484,235, filed Sep. 11, 2014, which claims priority to U.S. Provisional Patent Application No. 61/879,440, filed Sep. 18, 2013, the entire contents of each of which are hereby incorporated by reference.

TECHNICAL FIELD

The present disclosure provides a method for administration of a formulation of resiniferatoxin (RTX) to provide cardiac sympathetic afferent denervation when in an amount and concentration sufficient to chemically denervate vanilloid 1 receptor (TRPV1)-expressing CSAR (cardiac sympathetic afferent reflex) afferents. The present disclosure further provides a method for treating heart failure or hypertension and its related indications selected from the group consisting of increased sympatho-excitation, cardiac hypertrophy, increased left ventricular end diastolic pressure (LVEDP), lung edema, and combinations thereof, comprising administering an effective amount of RTX directly to a tissue site selected from the group consisting of epicardium, dorsal root ganglion T1-T4 and intrathecally to the T1-T4 region of the spinal column.

BACKGROUND

Chronic heart failure (CHF) is a serious and debilitating condition with poor survival rates and an increasing level of prevalence. Exaggerated sympatho-excitation, that is a hallmark of CHF, is a critical factor in the development and progression of CHF. Sympatho-excitation targets multiple organs and causes long-term effects that contribute to disease progression. The mechanism(s) by which sympathetic excitation occurs in the CHF state are not completely understood.

Myocardial ischemia causes the production and release of several metabolites including bradykinin, prostaglandins and protons that stimulate sympathetic afferent nerve endings. This leads to increases in arterial pressure (AP), heart rate (HR) and sympathetic nerve activity (Wang and Zucker, *Am. J. Physiol.* 1996, 271:R751-R756; Wang and Ma, *Heart Fail Rev.* 2000; 5:57-71; and Longhurst et al. *Ann. N Y Acad. Sci.* 2001; 940:74-95). In CHF, the CSAR is sensitized and cardiac sympathetic afferents are tonically activated (Wang and Zucker, *Am. J. Physiol.* 1996 271:R751-R756; Gao et al. *Hypertension.* 2005; 45:1173-1181; and Wang and Ma, *Heart Fail Rev.* 2000; 5:57-71).

Increased cardiac sympathetic nerve activity is a primary characteristic of patients suffering from CHF (Lohse et al. *Circ. Res.* 2003; 93:896-906; and Hasking et al. *Circulation.* 1986; 73:615-621). Prolonged stimulation of the f3-adrenergic neurohormonal axis has been shown to contribute to the progression of CHF and mortality in both animal models and in humans (Singh et al. *Cardiovasc. Res.* 2000; 45:713-719; and Fowler et al. *Circulation.* 1986; 74:1290-1302). Measurements of cardiac NE spillover in CHF patients reflecting cardiac sympathetic nerve activity, indicate that it is increased earlier and to a greater extent than sympathetic nerve activity to other organs (Ramchandra et al. *Proc. Natl. Acad. Sci. USA.* 2009; 106:924-928; Meredith et al. *N. Engl. J. Med.* 1991; 325:618-624; and Rundqvist et al. *Circulation.* 1997; 95:169-175). One potential explanation is an increased CSAR control of cardiac sympathetic efferent outflow (also called the "cardiac-cardiac reflex") in CHF.

Myocardial ischemia releases large amounts of metabolites including bradykinin, ATP, prostaglandins and protons that stimulate cardiac sympathetic afferent nerve endings and cause an excitatory response of MAP, HR and sympathetic nerve activity. Acute epicardial application of lidocaine, which blocked cardiac sympathetic afferent input, decreased baseline MAP, HR and RSNA in anesthetized CHF dogs and rats but not in sham animals, indicating that the CSAR is tonically activated and contributes to the elevated renal sympathetic nerve activity in CHF. The sites at which the CSAR is sensitized reside at both the afferent endings (Wang et al. *Am. J. Physiol.* 1999; 277:H812-H817) and in the central nervous system (Ma et al. *Am. J. Physiol.* 1997; 273:H2664-H2671).

Direct application of a vanilloid receptor agonist into the neuron cell body contained in a ganglion opens calcium channels in VR1-expressing neuronal perikarya, triggering a cascade of events leading to cell death. Vanilloid receptor-1 (VR1) is a multimeric cation channel prominently expressed in nociceptive primary afferent neurons (Caterina et al., *Nature* 89:8160824, 1997; Tominaga et al., *Neuron* 531-543, 1998). Activation of the receptor typically occurs at the nerve endings via application of painful heat (VR1 transduces heat pain) or during inflammation or exposure to vanilloids. Activation of VR1 by an agonist, such as resiniferatoxin or capsaicin, results in the opening of calcium channels and the transduction of pain sensation (Szalllasi et al., *Mol. Pharmacol.* 56:581-587, 1999.) After an initial activation of VR1, VR1 agonists desensitize VR1 to subsequent stimuli. This desensitization phenomenon has been exploited in order to produce analgesia to subsequent nociceptive challenge. For example, it has been shown that topical administration of resiniferatoxin (RTX), which is a potent vanilloid receptor agonist, at the nerve endings in the skin triggers a long-lasting insensitivity to chemical pain stimulation. Furthermore, it has been shown that both subcutaneous and epidural administration of the RTX produce thermal analgesia when administered to rats, with no restoration of pain sensitivity for over 7 days (Szabo et al., *Brain Res.* 840:92-98, 1999).

Resiniferatoxin (RTX) is used as the vanilloid receptor agonist. RTX is unlike structurally related phorbol esters because it acts as an ultrapotent analog of capsaicin, the pungent principle of the red pepper. RTX is a tricyclic diterpene isolated from *Eurphorbia resinifera*. RTX induces pain, hypothermia, and neurogenic inflammation; the acute responses are followed by desensitization to RTX and by cross-desensitization to capsaicin. A homovanillyl group is an important structural feature of capsaicin and the most prominent feature distinguishing resiniferatoxin from typical phorbol-related compounds. Naturally occurring or native RTX has the following structure:

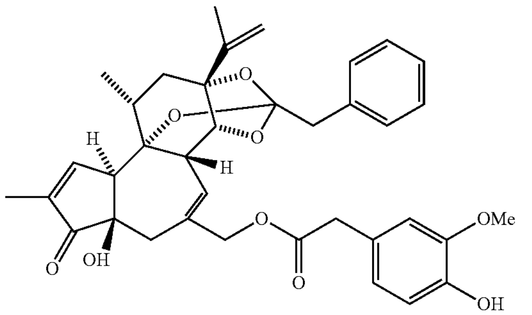 [SMILES: C=C(C)[C@]12C[C@@H](C)[C@@]34OC(Cc5ccccc5)(O[C@@H]1[C@@H]3C=C(COC(=O)Cc1ccc(O)c(OC)c1)C[C@]1(O)C(=O)C(C)=C[C@@H]41)O2]

RTX and analog compounds such as tinyatoxin as well other compounds, (20-homovanillyl esters of diterpenes such as 12-deoxyphorbol 13-phenylacetate 20-homovanillate and mezerein 20-homovanillate) are described in U.S. Pat. Nos. 4,939,194; 5,021,450; and 5,232,684, the disclosures of which are incorporated by reference herein. Other resiniferatoxin-type phorboid vanilloids have also been identified (Szallasi et al., *Brit. J. Phrmacol.* 128:428-434, 1999). As used herein, "a resiniferatoxin" or "an RTX" refers to naturally occurring RTX and analogs of RTX, including other phorbol vanilloids with VR1 agonist activity.

Transient receptor potential vanilloid 1 (TRPV1)-expressing cardiac afferent fibers are necessary for sensing and triggering the activation of the CSAR. Desensitizing cardiac afferents can almost completely abolish CSAR activation in adult rats (Zahner et al., *J. Physiol.* 2003; 551:515-523). Therefore, there is a need in the art to desensitize cardiac afferent fibers as a potential treatment for heart failure and its various related cardiovascular conditions.

SUMMARY

The present disclosure provides a method for administration of a formulation of resiniferatoxin (RTX) to provide cardiac sympathetic afferent denervation in an amount and concentration sufficient to chemically denervate vanilloid 1 receptor (TRPV1)-expressing CSAR (cardiac sympathetic afferent reflex) afferents. Preferably, the concentration of RTX administered is from about 100 ng/ml to about 500 µg/ml, preferably, from about 5 µg/ml to about 80 µg/ml, and most preferably from about 20 µg/ml to about 60 µg/ml. Preferably, in a human, the administration of RTX is accomplished by technique selected from the group consisting of pericardiocentesis, catheter based administration into the coronary artery circulation, intrathecal administration to a T1-T4 location and intraganglionic administration to a T1-T4 ganglion.

The present disclosure further provides a method for treating heart failure or hypertension and its related indications selected from the group consisting of increased sympatho-excitation, cardiac hypertrophy, increased left ventricular end diastolic pressure (LVEDP), lung edema, and combinations thereof, comprising administering an effective amount of RTX directly to a tissue site selected from the group consisting of epicardium, dorsal root ganglion and intrathecally to the T1-T4 region of the spinal column. Preferably, the concentration of RTX applied to the epicardium is from about 100 ng/ml to about 500 µg/ml, preferably, from about 5 µg/ml to about 80 µg/ml, and most preferably from about 20 µg/ml to about 60 µg/ml. Preferably, in a human, the administration of RTX is accomplished by technique selected from the group consisting of pericardiocentesis, catheter based administration into the coronary artery circulation, intrathecal administration to a T1-T4 location and intraganglionic administration to a T1-T4 ganglion.

The present disclosure further provides a method for preventing cardiac fibrosis following an MI, comprising administering RTX as soon as possible following an MI. Preferably, the concentration of RTX administered is from about 100 ng/ml to about 500 µg/ml, preferably, from about 5 µg/ml to about 80 µg/ml, and most preferably from about 20 µg/ml to about 60 µg/ml. Preferably, in a human, the administration of RTX is accomplished by technique selected from the group consisting of pericardiocentesis, catheter based administration into the coronary artery circulation, intrathecal administration to a T1-T4 location, and intraganglionic administration to a T1-T4 ganglion.

The present disclosure further provides a method for reducing cardiac inflammation in an infarcted heart, comprising administering RTX as soon as possible following an infarction. Preferably, the concentration of an RTX formulation administered is from about 100 ng/ml to about 500 µg/ml, preferably, from about 5 µg/ml to about 80 µg/ml, and most preferably from about 20 µg/ml to about 60 µg/ml. Preferably, in a human, the administration of RTX is accomplished by technique selected from the group consisting of peridcardiocentesis, catheter based administration into the coronary artery circulation, intrathecal administration to a T1-T4 location, and intraganglionic administration to a T1-T4 ganglion.

BRIEF DESCRIPTION OF DRAWINGS

FIGS. 3 B-D, western blotting data showing the protein expression of a-smooth muscle actin (α-SMA), fibronectin, transforming growth factor (TGF) beta 1 and β1-adrenergic receptors (β1-AR) in the left ventricle (remote region) and septum in sham+Vehicle, sham+RTX, CHF+Vehicle and CHF+RTX rats. Data are expressed as mean±SE. n=6/each group. *, P<0.05 vs. sham+vehicle, † P<0.05 vs. CHF+vehicle.

FIGS. 5 E and F, mean data showing the effect of RTX on the systolic (ESPVR, E) and diastolic (EDPVR, F) function that are independent of systemic vascular resistance in sham and CHF rats. Data are expressed as mean±SE. n=7-8/each group. *, P<0.05 vs. sham+vehicle, †, P<0.05 vs. CHF+vehicle.

DETAILED DESCRIPTION

Figure 1A:
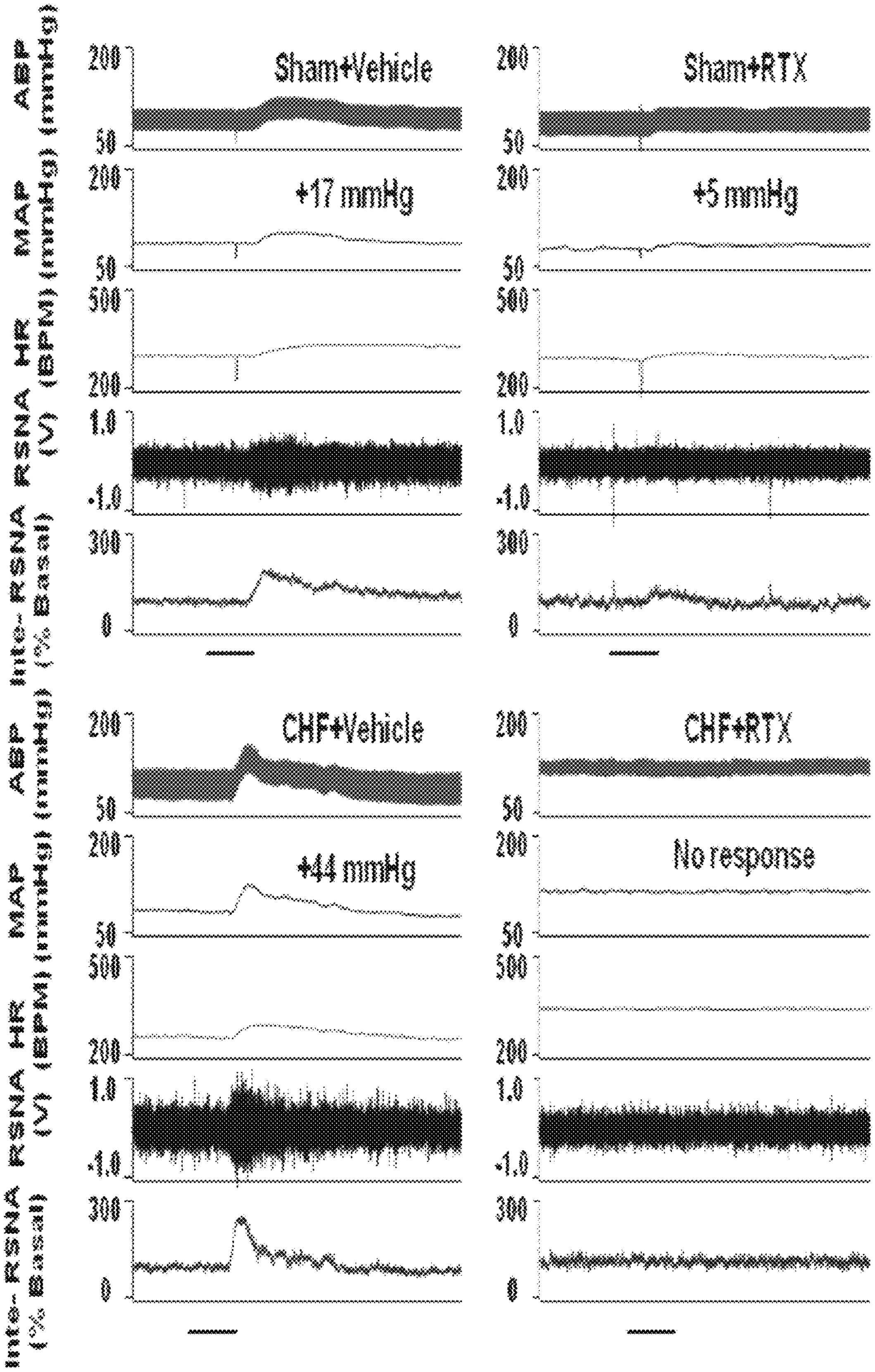
FIG. 1A-E show, (A) an original hemodynamic and neural recording, (B) and mean data showing the cardiovascular and (C) sympathetic responses to epicardial application of either capsaicin or bradykinin (10 µg/ml) in sham+vehicle, sham+RTX, CHF+Vehicle and CHF+RTX rats (n=8-12/each group). Scale bar in A represents 30 seconds. D and E, basal cardiac (n=6-8/each group) and renal sympathetic nerve activity (n=8-12/each group) and urinary NE secretion (E, n=6/each group) in sham+vehicle, sham+RTX, CHF+Vehicle and CHF+RTX rats. Values are mean±SE. *P<0.05 vs. sham+vehicle; †, P<0.05 vs. CHF+vehicle.
Figure 1B:
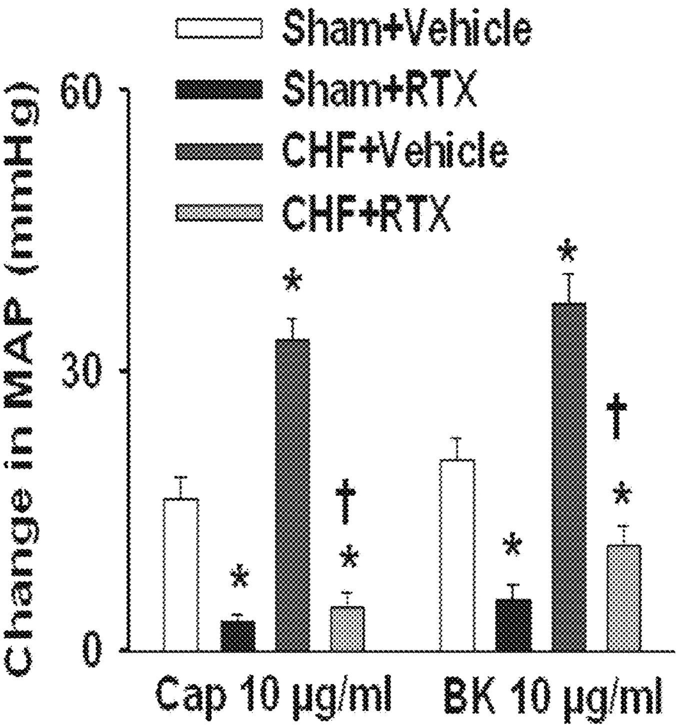
Figure 1C:
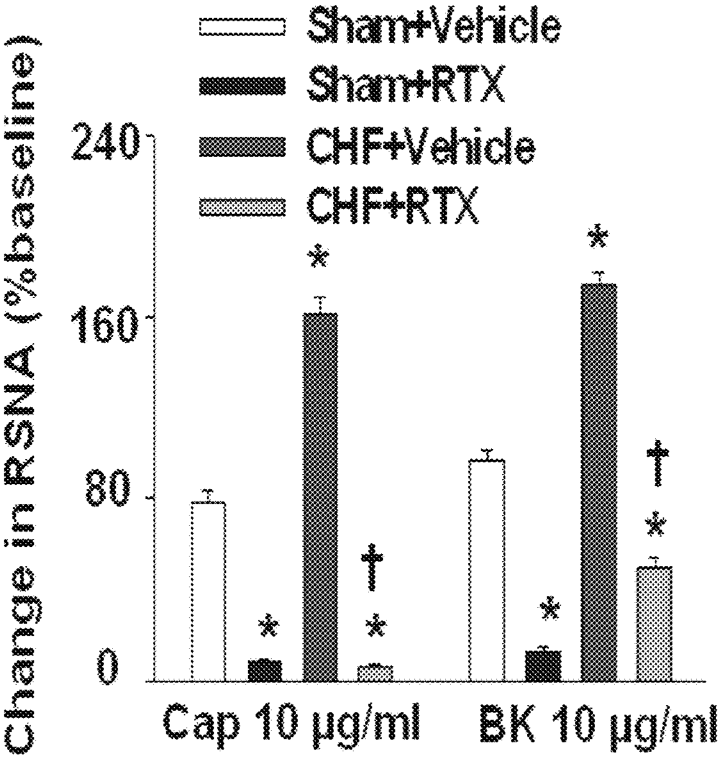

We performed epicardial application of RTX at the time of coronary ligation; MI surgery in rats in order to 1) investigate potential beneficial effects of selective deletion of TRPV1-expressing CSAR afferents on autonomic dysfunction and 2) determine whether the CSAR control of sympathetic nerve activity (especially cardiac sympathetic nerve activity; CSNA) plays a critical role in deleterious cardiac remodeling in CHF. Furthermore, we investigated the effects of CSAR afferent desensitization on cardiac morphological and hemodynamic function in rats with CHF. Epicardial administration of RTX comprises delivering RTX formulation to the epicardial surface, for example by using pericardiocentesis as a means for RTC delivery. Pericardiocentesis administration of RTX thereby selectively ablates cardiac sympathetic afferents in CHF patients. Therefore, the present disclosure shows that RTX-induced CSAR deafferentation prevents cardiac remodeling and reduces cardiovascular dysfunction in CHF rats and has high translational potential.

Definitions

The term "subarachnoid space" or cerebral spinal fluid (CSF) space incorporates the common usage refers to the anatomic space between the pia mater and the arachnoid membrane containing CSF.

The term "intrathecal administration" is the administration of a composition directly into the spinal subarachnoid space.

"Intraganglionic administration" is administration to a ganglion. Intraganglionic administration can be achieved by direct injection into the ganglion and also includes selective nerve root injections, in which the compound passes up the connective tissue sleeve around the nerve and enters the ganglion from the nerve root just outside the vertebral column. Often, intraganglionic administration is used in conjunction with an imaging technique, e.g., employing MRI or x-ray contrast dyes or agents, to visualize the targeted ganglion and area of administration.

"Epicardial administration" is administration to the surface of the epicardium or within the pericardial sac. An example of epicardial administration would be pericardiocentesis. Preferably, the site of epicardial administration is on the left ventricle.

"Pericardiocentesis" is administration into the pericardial space. Pericardiocentesis can be achieved by direct injection using a needle which is inserted through the pericardium into the pericardial space (space between the pericardium and epicardium). Often pericardiocentesis is used in conjunction with imaging techniques such as fluoroscopy or ultrasound.

In order to desensitize cardiac sympathetic afferents in rats, resiniferatoxin (RTX, 1 mg; Sigma Aldrich) was dissolved in 2 ml of ethanol and mixed with 18 ml of Tween in isotonic saline. RTX (50 μg/ml) was applied twice on the entire left and right ventricles with a swab just prior to coronary ligation. The dose of RTX was determined by preliminary experiments in which we found nearly complete ablation of TRPV1-expressing cardiac nerve endings on the surface of the rat heart for more than 10 weeks. Rat surgery was performed 9-11 weeks post-MI. Rats were anesthetized with urethane (800 mg/kg ip) and α-chloralose (40 mg/kg ip). Renal sympathetic nerve activity (RSNA) and cardiac sympathetic nerve activity (CSNA) were recorded for evaluating basal renal and cardiac sympathetic tone.

At the end of the experiment, the rat was euthanized with an overdose of pentobarbital sodium. The maximum cardiac or renal nerve activity (Max) occurred 1-2 min after the rat was euthanized. The background noise for sympathetic nerve activity was recorded 15-20 min after the rat was euthanized. Using the unit conversion function of the Powerlab Chart system, baseline nerve activity was determined as a percent of Max after the noise level was subtracted. The administration of RTX can be achieved through any medical implant/device including, but not limited to, catheters and drug-eluting stents. Administration may also be achieved through injection or may be administered during open surgery or by any other means necessary including, but not limited to, the use of swabs, sprays, or gels. Without being bound by theory, the postulated mechanism-of-action of RTX is inhibition of transient receptor potential villanoid type 1 receptor (TRPV1) on cardiac and nervous tissue.

This disclosure provides data from a rat model showing that topical epicardial application of RTX (by swab) at the time of myocardial infarction in rats causes decreased sympathetic nerve activation and an improvement in cardiac function after the establishment of chronic heart failure (6-8 weeks). Ablation of sensory nerve endings on the surface of the heart reduced sympatho-excitation that is a hallmark of chronic heart failure (CHF). RTX selectively ablated the Transient Receptor Potential Villanoid type 1 receptor (TRPV1) which is highly expressed in these nerve endings. Destruction of the TRPV1 receptor inactivated transmission of noxious stimuli by these receptors and lowered sympathetic nerve activity. In the disclosed experiments RTX was applied to the surface of the heart at the time of myocardial infarction surgery in rats. RTX had little effect in control rats but improved cardiac function and lowered sympathetic nerve activity in CHF rats. Therefore, (1) renal sympathetic nerve activity was reduced in RTX treated CHF rats; (2) arterial baroreflex function was enhanced in RTX treated CHF rats; (3) left ventricular end diastolic pressure was lower in RTX treated rats; and (4) ejection fraction decrease was less in RTX treated rats. Accordingly, RTX can lower sympathetic nerve activity in patients with severe CHF or in a hypertensive state.

The delivery of RTX is done in one of several ways. Epicardial administration in humans can be done by pericardiocentesis. Briefly, a needle is inserted through the pericardium through a trans-thoracic route under fluoroscopic or ultrasound guidance. Once in the pericardial space (between the pericardium and epicardium) RTX is delivered by syringe injection. RTX coats the surface of the heart and stimulates, then ablates cardiac sympathetic afferents, mainly in the left ventricle. In an adult human, approximately 20 ml can be injected (see: http://www.ncbi.nim.niti.govipmc/artieles/PMC3760565/). Other mammals will have more or less volume depending on their size relative to adult humans.

A second mode of administration is intracoronary. Injection by catheter into the main left coronary artery delivers a maximum dose to the left ventricle. Recirculated drug will be diluted in the peripheral circulation.

In another embodiment, RTX is administered into the intrathecal space at the level of the thoracic spinal cord (T1-T4) and is used to ablate dorsal root ganglion cells that express the TRPV1 channels; the molecular target of RTX.

RTX can also be injected directly into a ganglion or at the nerve root using standard neurosurgical techniques. Often, administration is performed using image analysis with MRI or x-ray contrast dyes, to provide for direct delivery to the perikarya. For example, the procedure can be performed in conjunction with procedures known in the art, such as CAT scan, fluoroscopy, or open MRI. RTX can also be administered intrathecally, typically in an isobaric or hyperbaric pharmaceutically acceptable excipient as further described below.

Typically, RTX administered to a particular ganglion (T1-T4) is administered to create a temporary environment from about 1 to 5 minutes. Multiple administrations can also be performed as required. For intraganglionic administration to a dorsal root or autonomic ganglion, a typical volume injected is from 50 to 300 microliters delivering a total amount of RTX that ranges from about 50 nanograms to about 50 micrograms. Often the amount administered is from 200 ng to 1 μg. RTX can be administered as a bolus or infused over a period of time, typically from 1 to 5 minutes. For intraganglionic administration to a trigeminal ganglion, a volume of from about 100 microliters to about 500 microliters is typically used to deliver from about 50 nanograms to about 50 micrograms of RTX. RTX can be infused over a length of time from about 1 to 5 minutes, or can be delivered as one or more boluses. Dosages in the ranges of 100 nanograms to 500 micrograms are often used. For intrathecal administration, an amount from about 0.5 to 5 ml, often 3 ccs are injected into the subarachnoid space. The total amount of RTX in the injected volume is usually from about 500 nanograms to about 500 micrograms.

The preferred dose for an adult human is about 25 μg of RTX for intrathecal administration. The preferred dose for intraganglionic administration for an adult human is about 5-20 μg. The volume administered for intrathecal administration is from about 0.5 mL to about 4.0 mL. The volume administered for intraganglionic administration is from about 100 μL to about 200 μL.

RTX Epicardial Administration

In a clinical setting, RTX is delivered to the surface of the heart using pericardiocentesis needle which is inserted under fluoroscopic or ultrasound guidance into the pericardial space to allow for direct injection of RTX and thereby selectively ablate cardiac sympathetic afferents in CHF patients.

RTX may also be administered into coronary arteries using a coronary artery catheter. Preferably, RTX is administered within a patch placed onto the epicardial surface for a slower release of RTX onto the epicardial surface.

Epicardial application of RTX, just prior to the creation of an MI (myocardial infarction or heart attack), abolished the enhanced CSAR, prevented the exaggerated renal and cardiac sympatho-excitation and increased the blunted baroreflex in CHF (congestive heart failure) rats. Epicardial application of RTX prevented many of the pathological indices of the CHF state. These included elevated LVEDP, lung edema, cardiac hypertrophy, chamber dilation and contractile reserve in response β-adrenergic receptor stimulation with ISO. RTX also ameliorated cardiac fibrosis and apoptosis in CHF rats.

Selective cardiac sympathetic afferent deafferentation by epicardial application of RTX prevented local excessive cardiac sympathetic activation in CHF rats. After blocking CSAR control of cardiac sympathetic activation by RTX, there were multiple improvements in the structure and function of the myocardium in CHF rats.

We examined multiple indices of cardiac remodeling and function in CHF rats treated with RTX. Our data show a reduction in chamber size, lower LVEDP, reduced cardiac hypertrophy, and attenuated cardiac fibrosis and apoptosis. Accordingly, there is RTX-mediated improvement in cardiac diastolic function in CHF rats. CHF rats treated with RTX did not exhibit the expected increase in LVEDP and lung congestion compared to CHF+vehicle rats. Our P-V loop data established a direct beneficial effect of RTX on cardiac diastolic function in the failing heart, independent of systemic vascular resistance. Furthermore, our molecular data suggest that RTX attenuated cardiac fibrosis in non-infarcted areas of the LV and IVS of CHF rats by reducing activation of the classic TGF-β receptor fibrotic signaling pathway. Taken together, these data suggest that the lower LVEDP observed in CHF+RTX rats is, at least in part, due to an RTX-mediated improvement of cardiac compliance. Because peripheral venous beds are highly innervated by sympathetic nerves and RTX-induced CSAR attenuation reduced the exaggerated systemic sympatho-excitation in CHF, another possibility is a reduction in venoconstriction and thus reduced cardiac filling, which would contribute to lower LVEDP in RTX-treated CHF rats.

RTX showed effects on cardiac systolic function in CHF. More particularly, favorable effects of RTX on $dp/dt_{max}$ were not evident in the basal (unstimulated) state, but rather in response to β-adrenergic receptor stimulation with ISO, indicating that myocardial contractile reserve was substantially increased after RTX treatment. This finding is consistent with the observation that the downregulation of n-AR in the myocardium of CHF rats was partially prevented by RTX. Without being bound by theory, by removing the influence of CSAR on sympathetic outflow to the heart and thereby reducing excessive myocardial NE release, an upregulation of the β-AR takes place.

RTX treatment affected remodeling processes in other ways. For example, in CHF+RTX rats, LV (left ventricle) chamber size was smaller as reflected by reduced LV end-systolic and end-diastolic diameters and volumes compared to CHF+vehicle rats even when ejection fraction and infarct size were similar. During progression of CHF, persistent ischemia and inflammation in an ischemic zone impair granulation tissue, extracellular matrix formation (ECM) and ischemic myocyte survival, resulting in extension and expansion of the failing myocardium. Epicardial RTX applied at the time of MI creation reduces this vicious cycle and delays progression of the CHF state.

RTX significantly ameliorated cardiac apoptosis in both infarcted and non-infarcted areas of left ventricle in CHF rats. The CSAR is a sympatho-excitatory reflex and contributes to an elevation in sympathetic tone. The latter can antagonize baroreflex function in the CHF state. Epicardial application of RTX at the time of MI creation prevented blunted baroreflex control of HR and RSNA 9-11 weeks post-MI, suggesting a chronic interaction between the CSAR and the baroreflex in CHF.

RTX was selectively delivered to the epicardium to ablate the TRPV1-expressing cardiac afferents. Therefore, it appears that RTX selectively targeted cardiac sympathetic afferents without impairing cardiac sympathetic and parasympathetic efferent nerves and vagal afferent nerves. The present disclosure provides multiple beneficial therapeutic effects of RTX-induced inhibition of the CSAR on cardiac and autonomic function in CHF rats.

In contrast to the present disclosure, genetic knockout techniques to systemically delete TRPV1 receptors in mice, have reported conflicting findings (Thilo et al. *Biochem. Biophys. Res. Commun.* 2010; 401:98-103; Huang et al. *Hypertension* 2009; 53:243-250; Horton et al. *Channels* (Austin). 2013; 7:17-22; and Buckley and Stokes, *Channels* (Austin). 2011; 5:367-374) concerning either the beneficial or deleterious effects of global deletion of TRPV1 on cardiac function. There are several major differences between selective TRPV1-expressing cardiac afferent ablation and systemic pharmacological antagonism or genetic deletion of TRPV1 receptor strategies. RTX not only deleted TRPV1 receptors in cardiac afferents but also damaged TRPV1-expressing nerve endings rather than only blocking TRPV1 receptors. Considering that TRPV1-expressing cardiac sympathetic afferent endings also express many other sensory receptors, such as tachykinin and purinergic receptors, RTX also impaired these sensory receptors following damage of TRPV1-expressing cardiac afferent nerve endings. Without being bound by theory, this explains why epicardial RTX application blocks both epicardial capsaicin and bradykinin-induced cardiovascular responses whereas TRPV1 receptor blockade using epicardial ido-RTX only abolishes epicardial capsaicin-induced responses without any effect on the bradykinin-induced cardiovascular response.

Epicardial application of RTX was performed at the time of MI rather than several days or weeks after MI. Therefore, beneficial effects of RTX on cardiac and autonomic function indicate an early protective effect against progress of deleterious cardiac remodeling in post-MI rats. Epicardial application of RTX during MI or very early post-MI in rats had greater protective effects on cardiac dysfunction than during the mid or late post-MI period. Therefore, the present disclosure provides a method for preventing cardiac fibrosis following an MI, comprising administering RTX to the epicardium as soon as possible following an MI.

When applying a higher concentration (50 μg/ml) of RTX to the surface of heart, we abolished CSAR for at least 9-11 weeks. We did observe a recovery of CSAR sensitivity at 6 months after epicardial application of RTX, indicating that in a clinical setting this may need to be repeated.

In summary, the present disclosure provides evidence demonstrating that selective cardiac sympathetic afferent deafferentation by epicardial application of RTX during MI prevents cardiac and autonomic dysfunction in rats 9-11 weeks post MI.

Example 1

This example shows that RTX causes loss of TRPV1-expressing cardiac afferents. More specifically, we examined TRPV1 protein expression in cardiac nerve endings from vehicle and RTX-treated rats using immunofluorescence. Experiments were performed on male Sprague-Dawley rats weighing −400 to −500 g. In brief, terminal experiments were carried out 9-11 weeks after MI in rats treated with either RTX or vehicle. These experiments were approved by the Institutional Animal Care and Use Committee of the University of Nebraska Medical Center and carried out under the guidelines of the National Institutes of Health *Guide for the Care and Use of Laboratory Animals*. Heart failure was produced by coronary artery ligation as described in (Wang et al., *J. Appl. Physiol.* 2010; 108:1365-1375; and Wang et al. 2, *Am. J. Physiol. Regul. Integr. Comp. Physiol.* 2012; 320:R1260-R1270). Cardiac function in all experimental animals was measured 2 and 6 weeks after MI by echocardiography (VEVO 770, Visual Sonics, Inc.) as described in (Wang et al., *J. Appl. Physiol.* 2010; 108:1365-1375; Wang et al. 2, *Am. J. Physiol. Regul. Integr. Comp. Physiol.* 2012; 320:R1260-R1270; and Wang et al. 3, *J. Physiol.* 2010; 588:5033-5047).

In vehicle-treated rats, TRPV1 immunoreactivity was primarily located to the epicardial surface and co-expressed with PGP 9.5 (a nerve terminal marker). In RTX-treated rats, TRPV1 immunoreactivity was absent in the epicardium when it was measured 1 week, 4-6 weeks and 9-11 weeks after epicardial application of RTX (50 μg/ml), respectively. These data suggest effective deletion of TRPV1-expressing cardiac afferents during these periods.

In another parallel set of experiments, we further confirmed the efficiency of RTX-induced TRPV1-expressing CSAR afferent ablation functionally by epicardial application of capsaicin and bradykinin (10 μg/ml) in sham+RTX rats treated with various doses (0.5 μg/ml, 5 μg/ml and 50 μg/ml) and at various time points (1 week, 4-6 weeks, 9-11 weeks and 6 months after RTX). These data show that both epicardial application of 5 μg/ml and 50μ/ml RTX largely abolished the cardiovascular responses to acute epicardial application of capsaicin and bradykinin 1 week after RTX in sham rats. However, in the preliminary experiment, we observed that 40% of sham rats that were treated with epicardial application of RTX at a dose of 5 μg/ml showed partial recovery of the cardiovascular responses to acute epicardial application of capsaicin and bradykinin 10 weeks after RTX whereas all rats treated with 50 μg/ml RTX were still insensitive to capsaicin and bradykinin at this time point. Therefore, a higher dose greater than 5 μg/ml should be used for epicardial administration.

We used 50 μg/ml RTX in all following experiments. Data from time course experiments demonstrated that epicardial application of this dose (50 μg/ml) of RTX effectively abolished cardiovascular responses to acute epicardial application of capsaicin and bradykinin for more than 10 weeks whereas these cardiovascular responses to capsaicin and bradykinin were largely recovered at 6 months after RTX.

Example 2

This example illustrates functional experiments comparing RTX-treated sham and CHF rats 9-11 weeks after RTX administration (50 μg/ml) was carried out. As shown in FIG. 1A-1E, compared to sham+vehicle rats, CHF+vehicle rats exhibited exaggerated MAP, HR and renal sympathetic nerve activity (RSNA) responses to epicardial application of either capsaicin or bradykinin. However, the cardiovascular and sympathetic activation in response to epicardial capsaicin in both sham and CHF rats were almost completely abolished by epicardial pretreatment with RTX (50 μg/ml).

To determine activation of the CSAR, epicardial application of capsaicin and bradykinin was used to effectively stimulate the cardiac sympathetic afferents (Zahner et al. *J. Physiol.* 2003; 551:515-523). The time interval between capsaicin and bradykinin was about 15-20 min to allow the arterial pressure (AP), heart rate (HR) and renal sympathetic nerve activity (RSNA) to return to, and stabilize at their control levels. RTX also greatly attenuated bradykinin-induced CSAR activation in both sham and CHF rats.

Example 3

This example illustrates an effect of RTX on body weight, organ weight, and hemodynamics in sham and CHF rats. Morphological and hemodynamic measurements of the groups of rats are summarized in Table 1.

Hemodynamic and echocardiographic measurements point to several other differences between CHF+vehicle and CHF+RTX rats. CHF+vehicle rats exhibited elevated left ventricle end-diastolic pressure (LVEDP; i.e. a reflection of the total volume that remains in the left ventricle at the end of cardiac contraction and the strength of contraction) and time-dependent decline in ejection fraction and fractional shortening compared with sham+vehicle rats (Table 1), indicating decreased ventricular function. However, the increased LVEDP observed in CHF+vehicle rats was largely prevented in CHF+RTX rats, which is consistent with the finding that lung congestion was also reduced in CHF+RTX rats. MI-induced cardiac dilation in CHF rats, indicated by increased LV systolic and diastolic diameters and volumes, was significantly reduced by RTX treatment compared to sham rats. Interestingly, although LVEDP and cardiac dilation were reduced by RTX, there was no significant difference in ejection fraction or fractional shortening 2 weeks and 6 weeks after MI between CHF+RTX and CHF+vehicle rats.

Figure 2A:
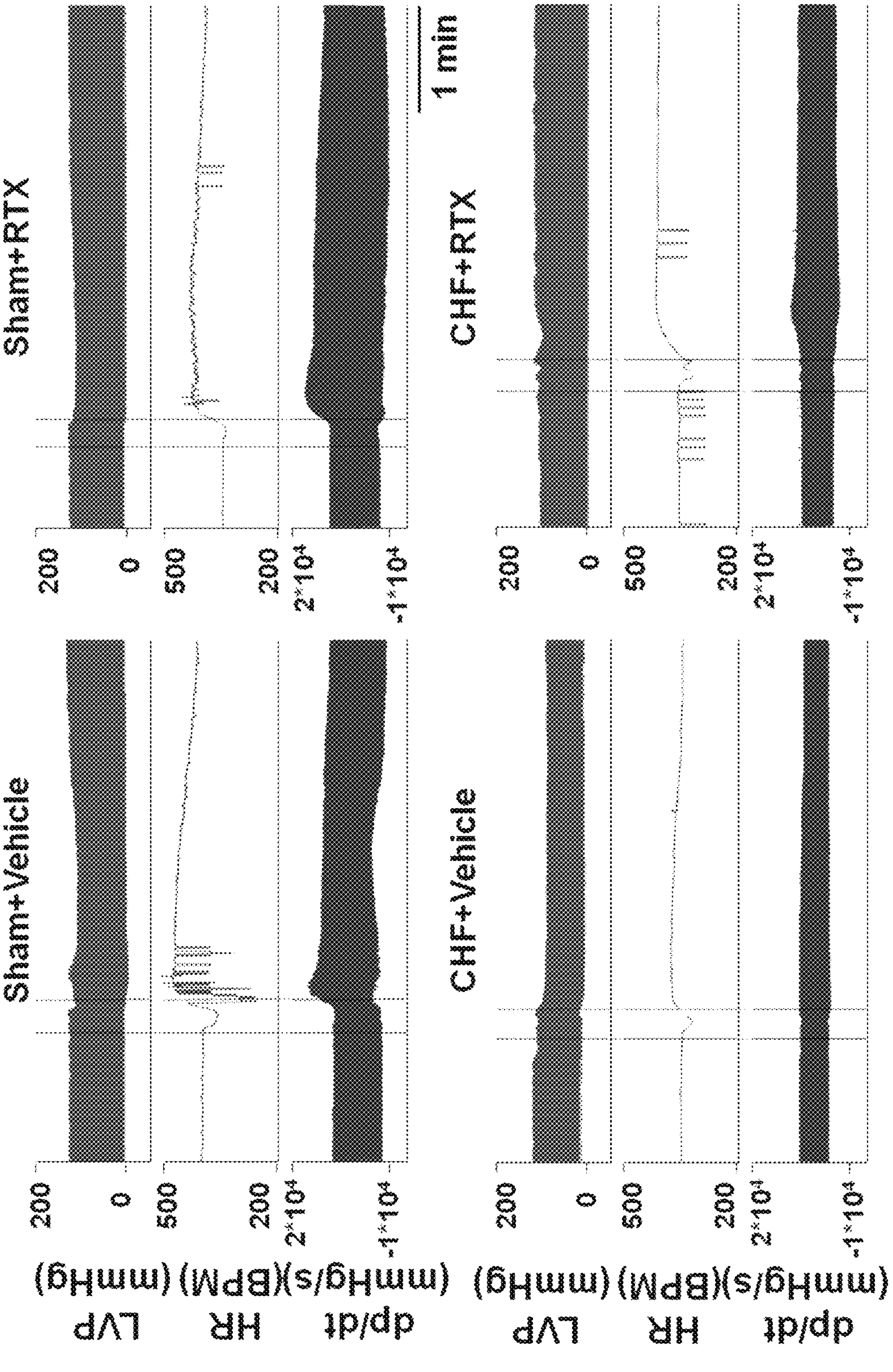
FIGS. 2A and B shows representative recordings (A) and mean data (B) showing basal dp/dtmax and diastolic dp/dtmin as well as the dose-dependent responses to beta-adrenergic receptor stimulation with ISO (0.01, 0.1 and 1.01 mg/kg, 0.2 ml). Values are mean±SE. n=6/each group. *P<0.05 vs. sham+vehicle; †, P<0.05 vs. CHF+vehicle.
Figure 2B:
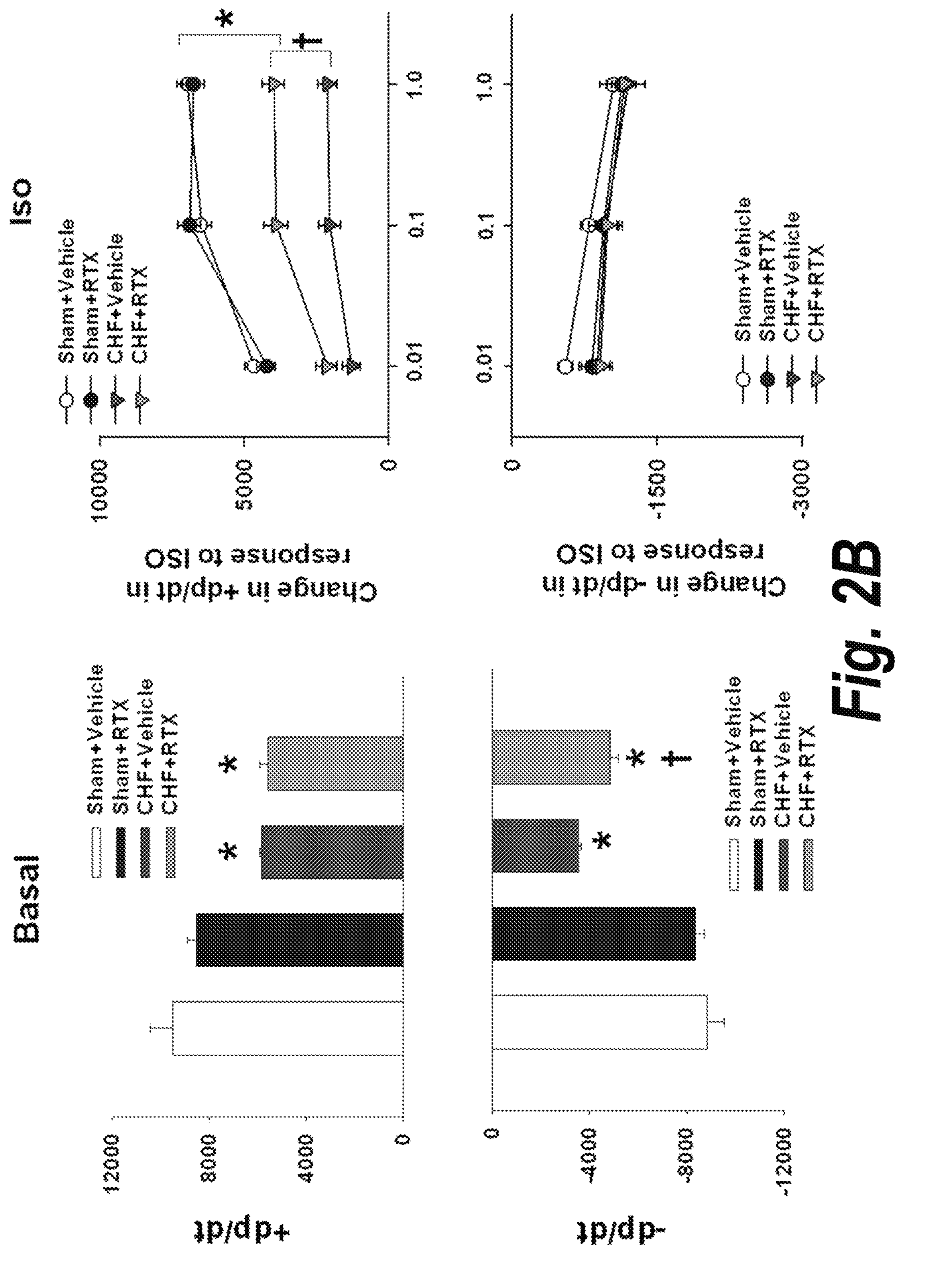

Dp/dt measurements (Table 1 and FIG. 2) further showed differences between CHF+vehicle and CHF+RTX rats. Compared to sham+vehicle rats, CHF+vehicle rats exhibited decreased $dp/dt_{max}$ and $dp/dt_{min}$ suggesting both systolic and diastolic dysfunction in the hearts of CHF rats (Table 1). However, the blunted $dp/dt_{min}$ in CHF+vehicle rats was significantly increased in CHF+RTX rats, potentially indicating improved diastolic function in CHF+RTX rats. Although there was no significant difference in $dp/dt_{max}$ at rest between CHF+RTX and CHF+vehicle rats, the $dp/dt_{max}$ response to isoproterenol (ISO) stimulation in CHF+RTX rats was significantly greater compared to CHF+vehicle rats (FIGS. 2A and B). At the molecular level, the decreased protein expression of β1-AR in myocardium of CHF+vehicle rats was partially reversed in CHF+RTX rats (FIG. 3D). There were no significant differences in cardiac morphological, echocardiographic or hemodynamic parameters between sham+vehicle and sham+RTX rats.

TABLE 1

Hemodynamic and morphological data in sham and CHF rats following vehicle or RTX treatment

| Parameters | Sham + Vehicle (n = 21) | Sham + RTX (n = 20) | CHF + Vehicle (n = 23) | CHF + RTX (n = 25) |
|---|---|---|---|---|
| Body weight, g | 429 ± 7 | 430 ± 7 | 452 ± 8 | 440 ± 8 |
| Heart weight, mg | 1438 ± 28 | 1430 ± 30 | 2239 ± 61* | 1650 ± 49*† |
| HW/BW, mg/g | 3.4 ± 0.1 | 3.3 ± 0.1 | 5.0 ± 0.1* | 3.8 ± 0.1*† |
| WLW/BW, mg/g | 4.4 ± 0.1 | 4.5 ± 0.1 | 8.7 ± 0.3* | 5.1 ± 0.2*† |
| SAP, mmHg | 127.9 ± 2.2 | 128.8 ± 2.8 | 115.3 ± 2.0* | 120.8 ± 2.3* |
| MAP, mmHg | 103.5 ± 2.4 | 105.0 ± 3.1 | 96.7 ± 2.0* | 101.3 ± 2.1 |
| DAP, mmHg | 91.6 ± 2.5 | 92.8 ± 3.2 | 87.3 ± 2.2 | 90.8 ± 2.2 |
| LVEDP mmHg | 5.0 ± 0.4 | 4.8 ± 0.4 | 21.3 ± 1.0* | 8.3 ± 0.7*† |
| HR, bpm | 357.3 ± 6.1 | 362.0 ± 6.8 | 368.9 ± 5.1 | 348.3 ± 5.5† |
| $dp/dt_{max}$ | 9108 ± 324 | 8601 ± 224 | 5137 ± 180* | 5446 ± 173* |
| $dp/dt_{min}$ | −8458 ± 235 | −8088 ± 196 | −3452 ± 113* | −4643 ± 149*† |
| Infarct size, % | 0 | 0 | 42.5 ± 1.4* | 39.1 ± 1.2* |

Values are mean ± SE. BW, body weight; HW, heat weight; WLW, wet lung weight; LVEDP, left ventricle end-diastolic pressure; SAP, systolic arterial pressure; MAP, mean arterial pressure; DAP, diastolic arterial pressure; HR, heart rate.
*P < 0.05 vs. sham + Vehicle.
†P < 0.05 vs. CHF + Vehicle.

The heart weight and lung weight-to-body weight ratios were significantly higher in CHF+vehicle rats compared to sham+vehicle rats, suggesting cardiac hypertrophy and pulmonary congestion in the CHF state. However, after pretreatment with epicardial RTX, there was a significant decrease in both the heart weight and lung weight-to-body weight ratios in CHF rats compared to CHF+vehicle rats, suggesting a protective effect of RTX on cardiac hypertrophy and pulmonary congestion. There was no significant difference in infarct size between CHF+vehicle and CHF+RTX rats (Table 1), which excludes the possibility that the variability in infarct size caused the difference in the heart weight or lung weight between CHF+vehicle and CHF+RTX rats.

Example 4

This example illustrates the effects of RTX on cardiac fibrosis in sham and CHF rats. Considering that RTX-mediated reduction in LVEDP in CHF rats may be related to an improvement in cardiac compliance, we further evaluated cardiac fibrosis using picrosirius red staining and protein expression of two fibrotic markers (a smooth muscle actin and fibronectin) as well as their upstream activator, transforming growth factor (TGF) β receptor I in the non-infarcted LV and inter-ventricular septum (IVS) walls from sham and CHF rats treated with either vehicle or RTX. For histopathology, the rat heart was fixed in 10% phosphate buffered formalin, embedded in paraffin, and cut into 10 μm serial sections from apex to base. Picrosirius red staining was performed to detect myocardial fibrosis Immunohistochemistry staining of cleaved caspase 3 (CC3) was also performed in paraffin sections from the same heart tissues which were used for picrosirius red staining experiments.

Figure 3A:
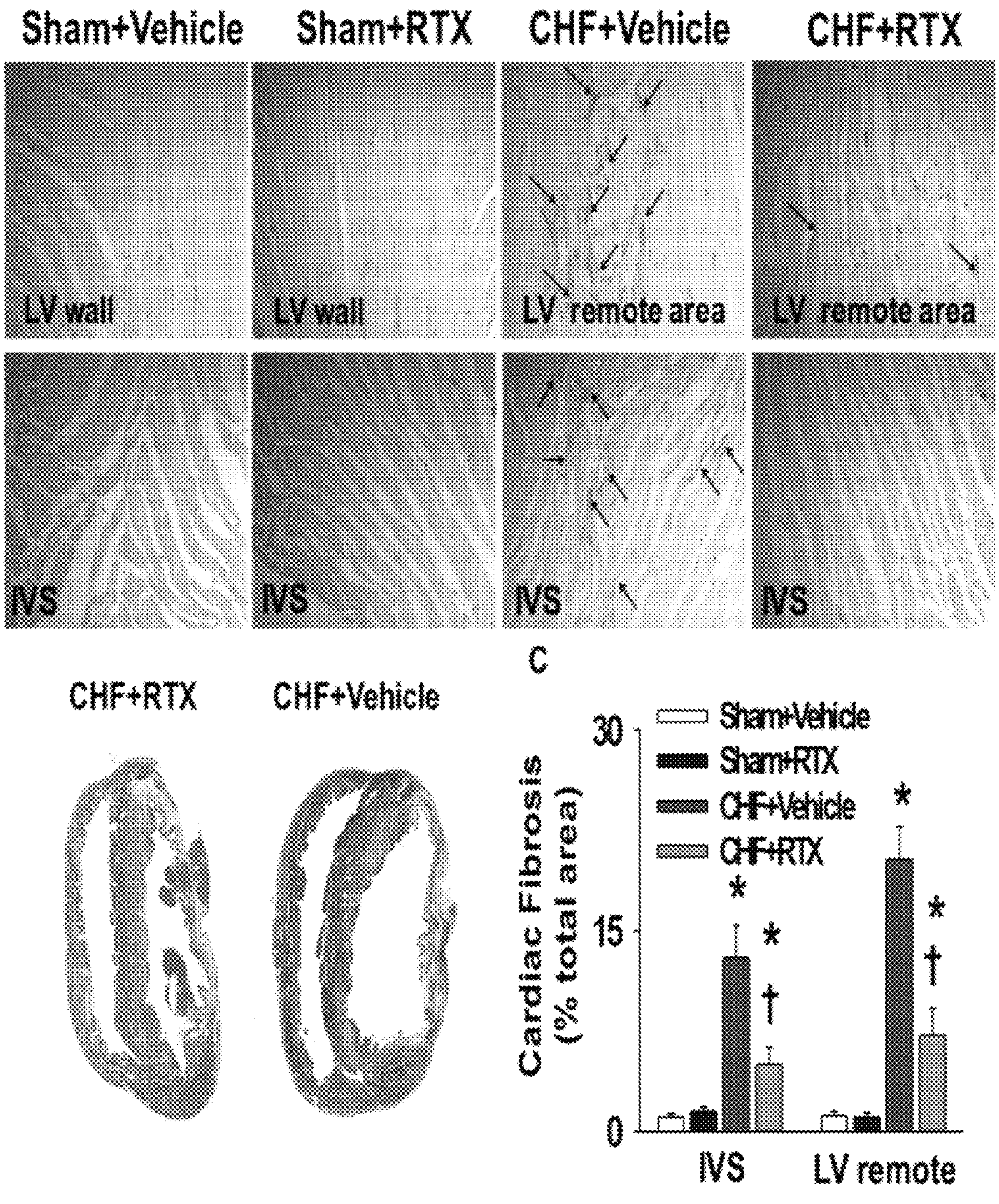
FIG. 3A-D shows A, representative sirius red stain (top) and mean data (bottom right) showing that RTX reduces cardiac fibrosis induced by myocardium infarction (MI); bottom left, Masson's trichrome staining showing similar infarcted size between CHF+Vehicle and CHF+RTX rats in top panel. Black arrows point to the sirius red-positive staining.
Figure 3B:
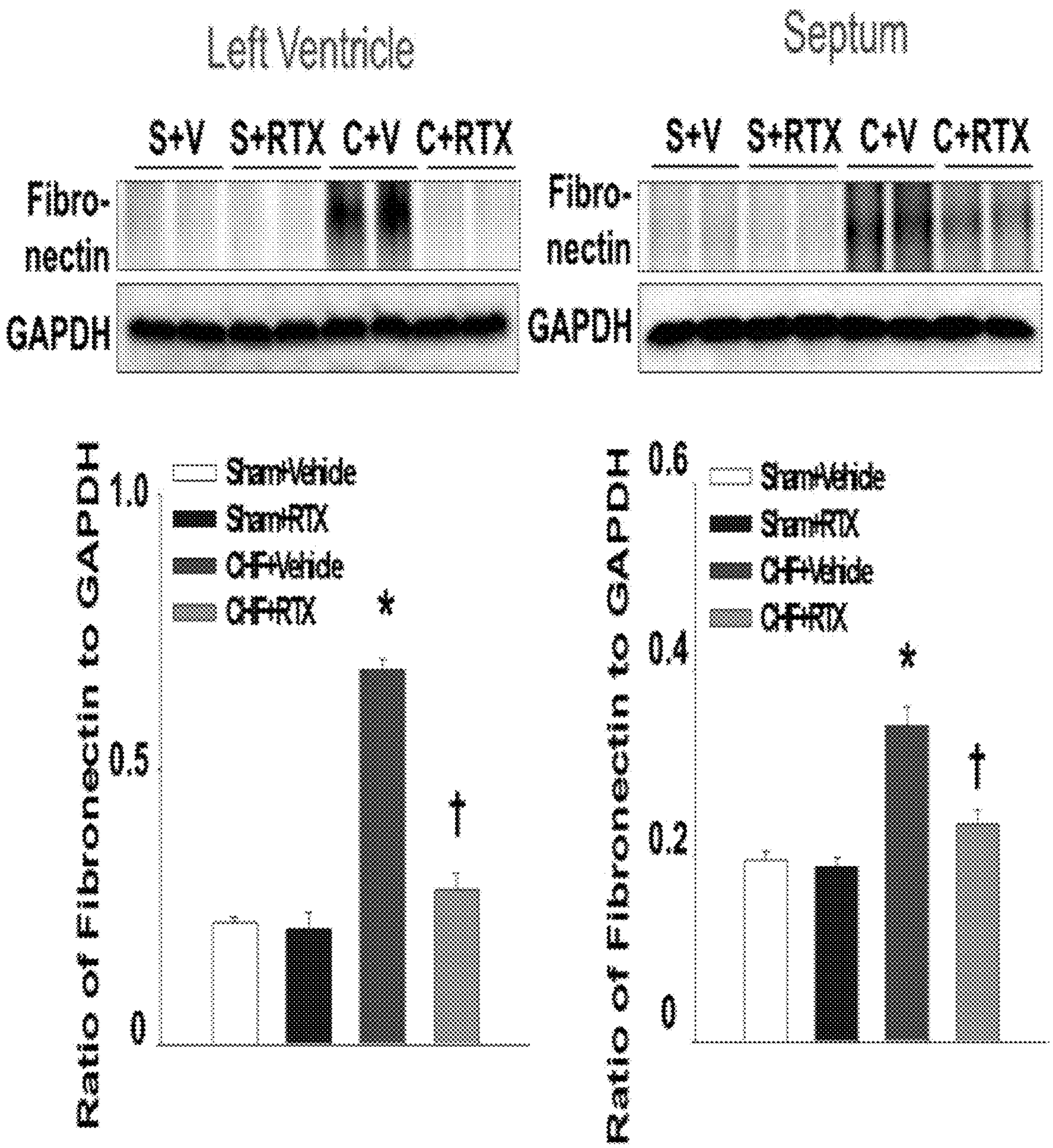
Figure 3C:
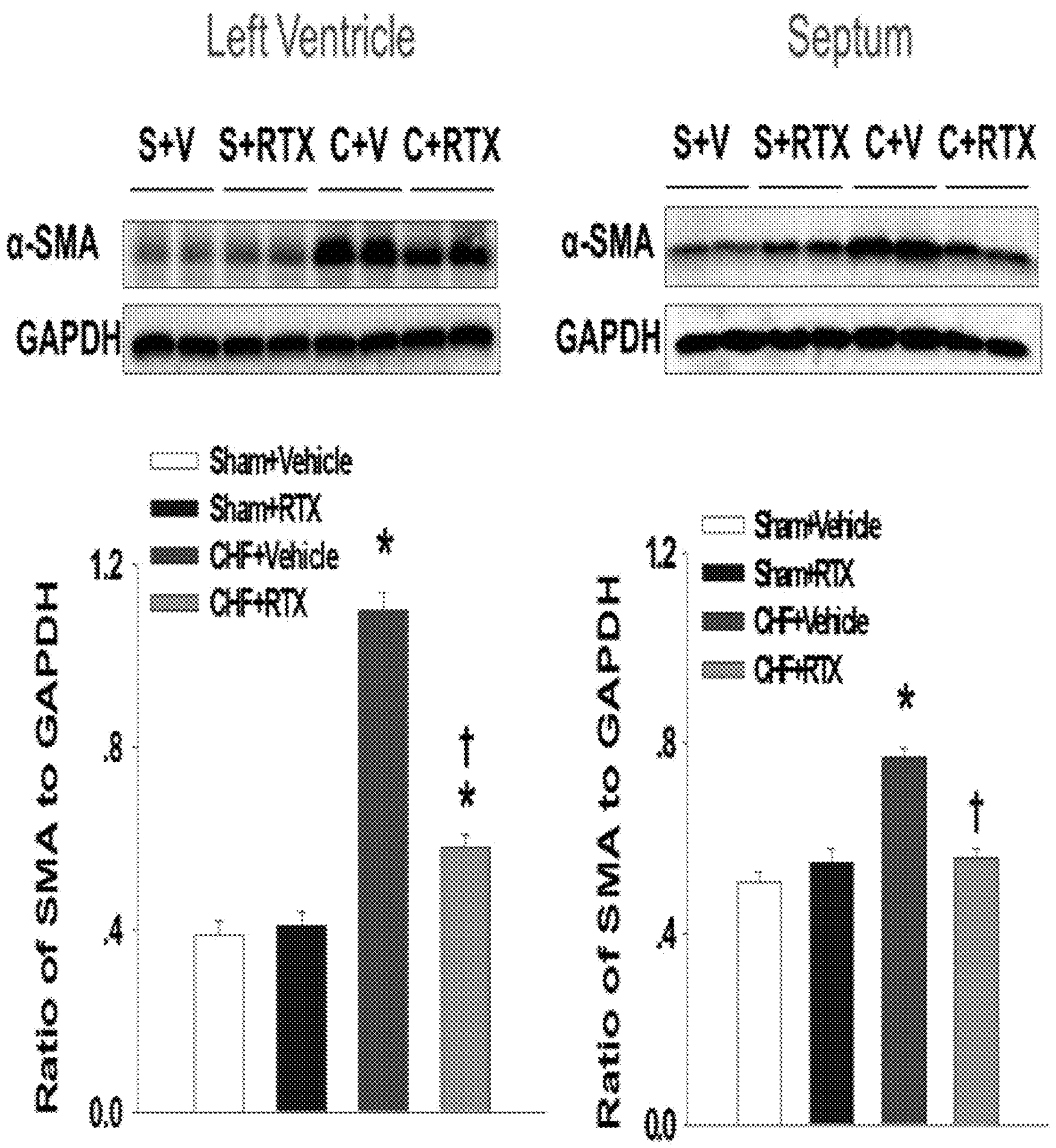
Figure 3D:
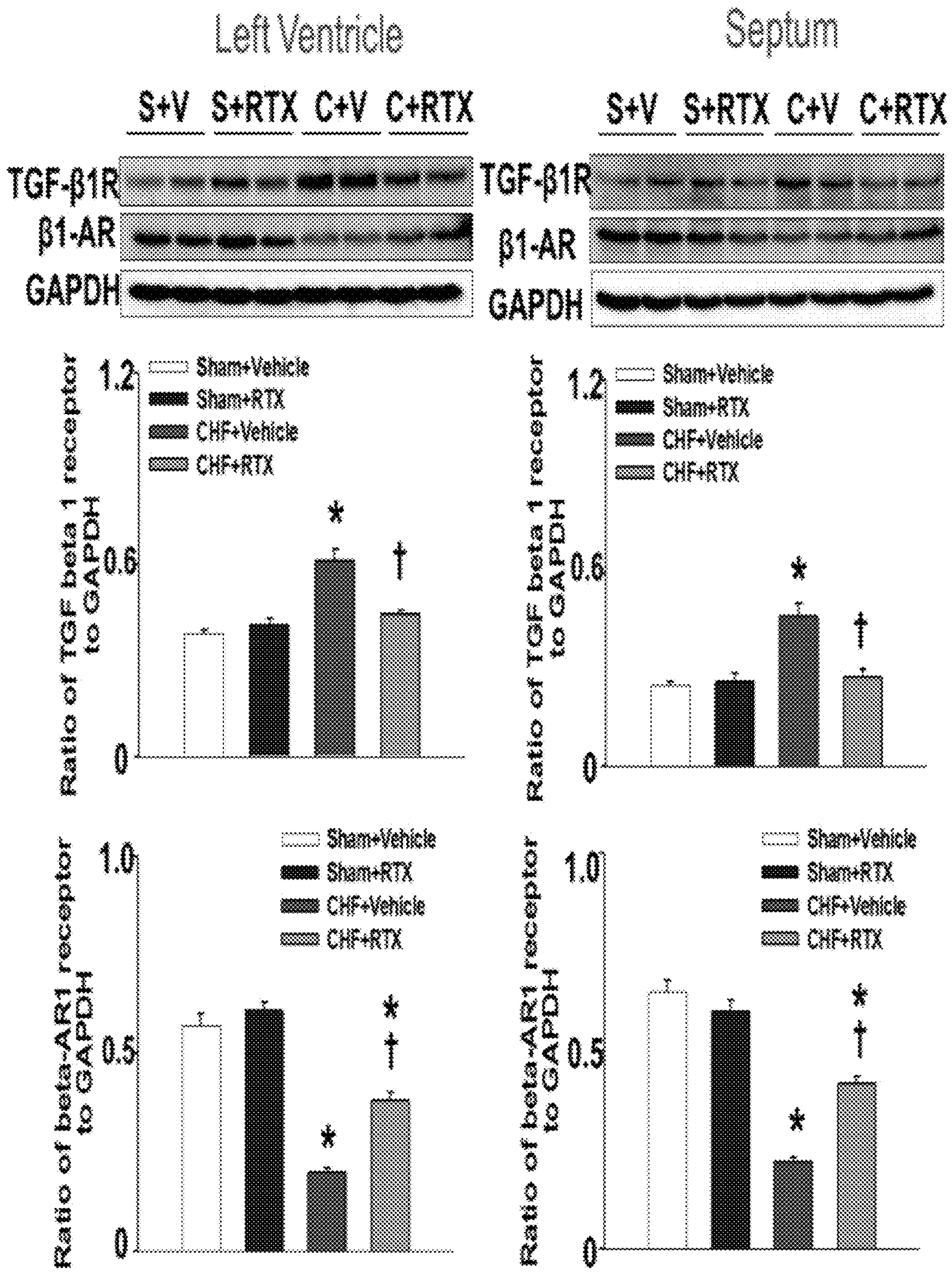

These data show that picrosirius red staining was increased in CHF+vehicle treated rats compared to sham rats (FIG. 3A). Alpha smooth muscle actin, fibronectin and TGF β receptor I were increased in CHF+vehicle rats (FIG. 3B-3D). RTX treatment in CHF rats reduced the expression of all these markers in the non-infarcted LV and IVS walls (FIG. 3A-D). RTX did not cause any significant change in either picrosirius red staining or protein expressions of fibrotic markers and TGF β receptor I in non-infarcted LV and IVS walls in sham rats (FIG. 3A-D).

Example 5

This example illustrates an effect of RTX on basal sympathetic tone and arterial baroreflex function in sham and CHF rats. Baroreflex curves were generated by measuring HR and RSNA responses to decreases and increases in AP by intravenous administration of nitroglycerin (25 μg) followed by phenylephrine (10 μg) as previously described (Gao et al. *Hypertension* 2005; 45:1173-1181).

Figure 1D:
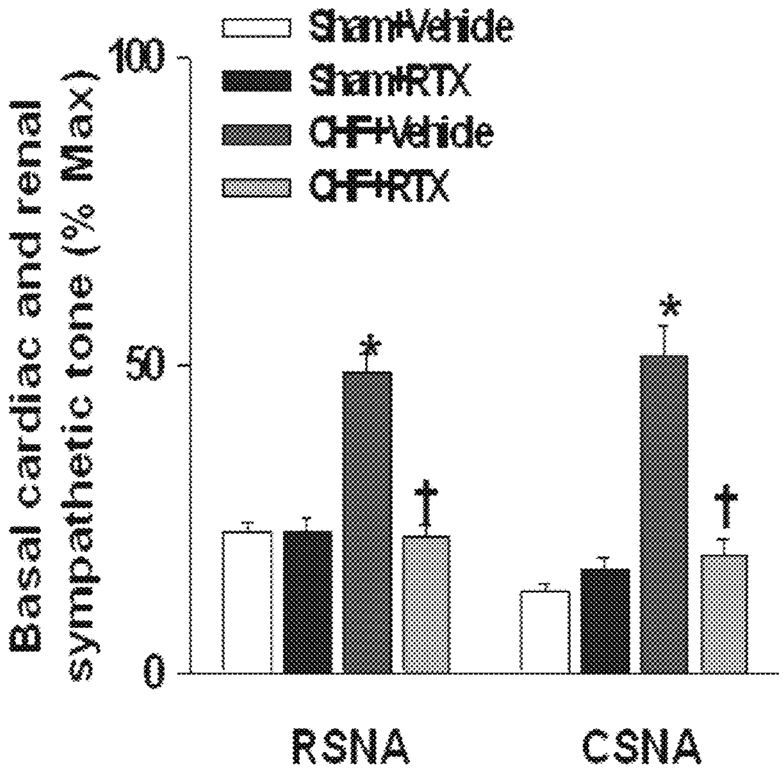
Figure 1E:
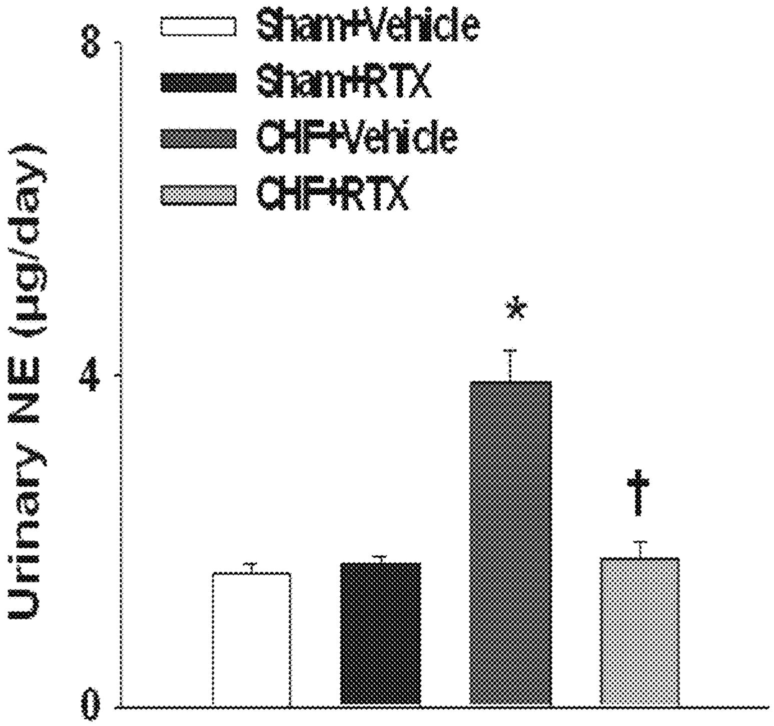
Figure 4A:
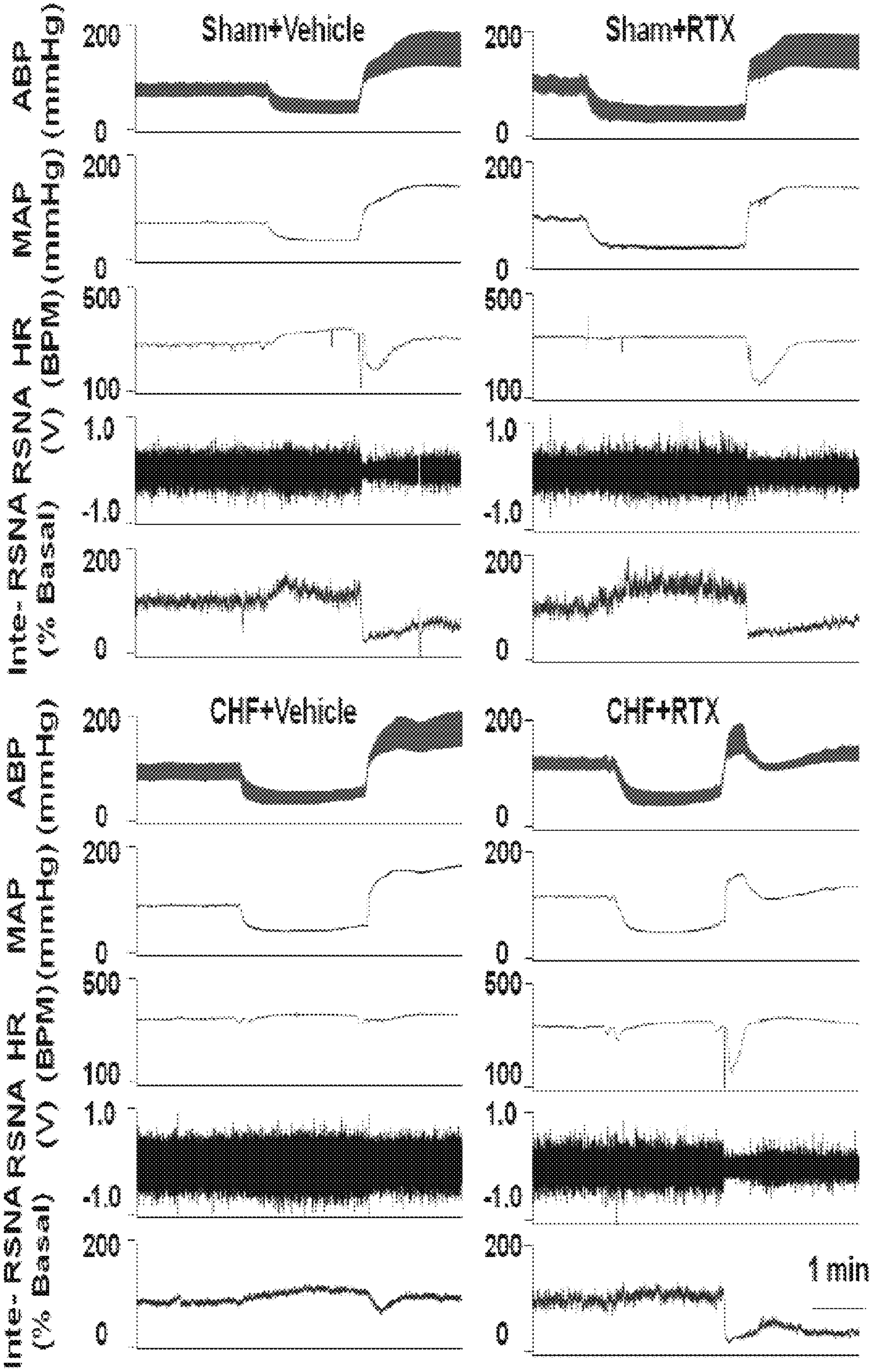
FIG. 4A-C shows original recordings (A) and mean data (B,C) showing baroreflex curves and gain in sham+vehicle, sham+RTX, CHF+Vehicle and CHF+RTX rats. Data are expressed as mean±SE. n=8-10/each group. * P<0.05 vs. sham+vehicle and sham+RTX and CHF+RTX.
Figure 4B:
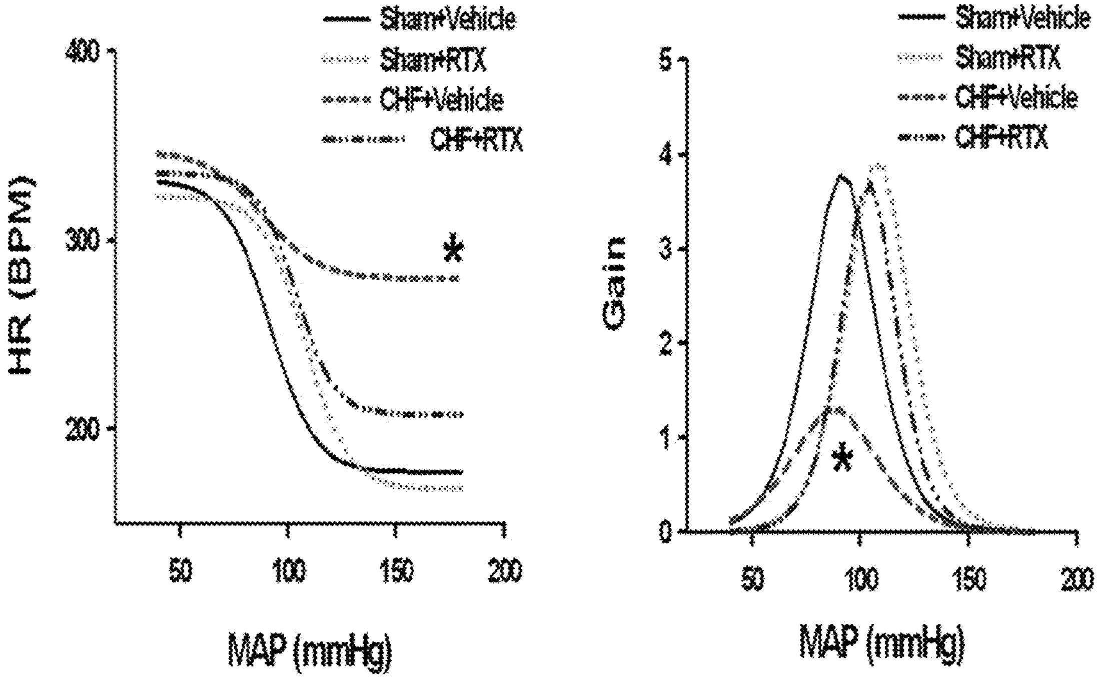
Figure 4C:
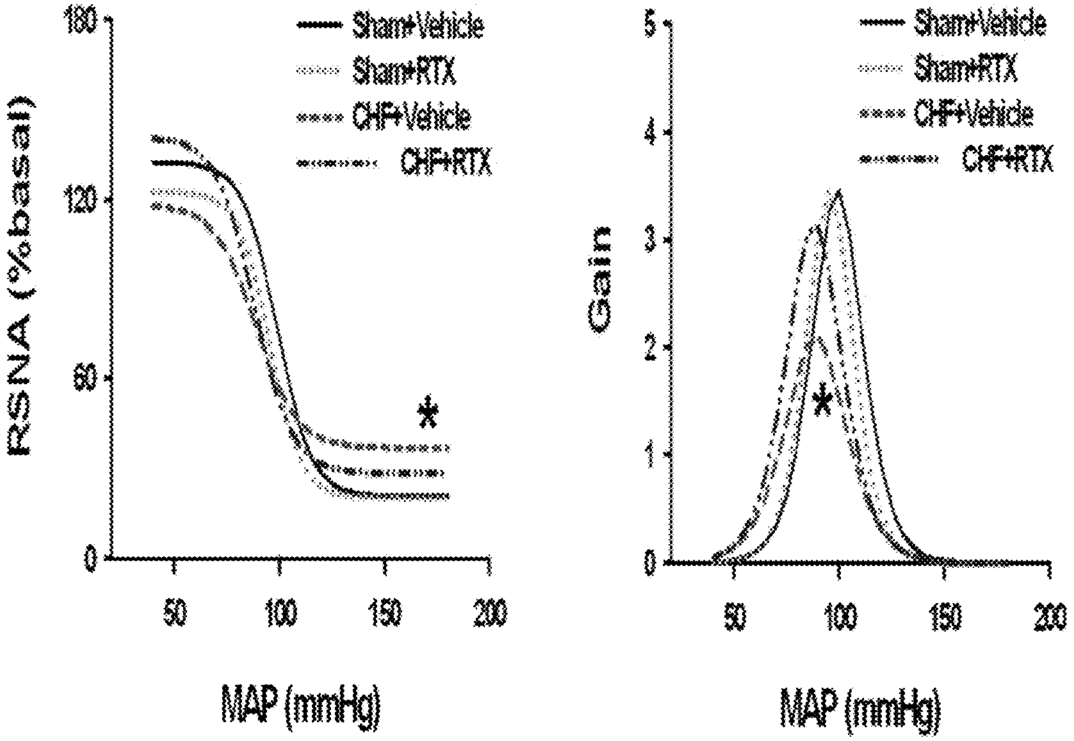

Baseline RSNA and CSNA were significantly higher in CHF+vehicle rats compared to sham+vehicle rats, indicating increased renal and cardiac sympathetic tone in CHF. RTX lowered basal RSNA and CSNA in CHF rats (FIG. 1D). Furthermore, urinary NE excretion was significantly reduced in CHF+RTX rats compared to vehicle treated rats (FIG. 1E). In addition, RTX significantly increased the average slope and $Gain_{max}$, and decreased the minimum HR and RSNA of the arterial baroreflex control of both HR and RSNA (FIG. 4A-C). In contrast to the CHF rats, there were no significant effects on the average slope, $Gain_{max}$, and minimum RSNA or HR of arterial baroreflex control in sham rats (FIG. 4A-C).

Example 6

Figure 5A:
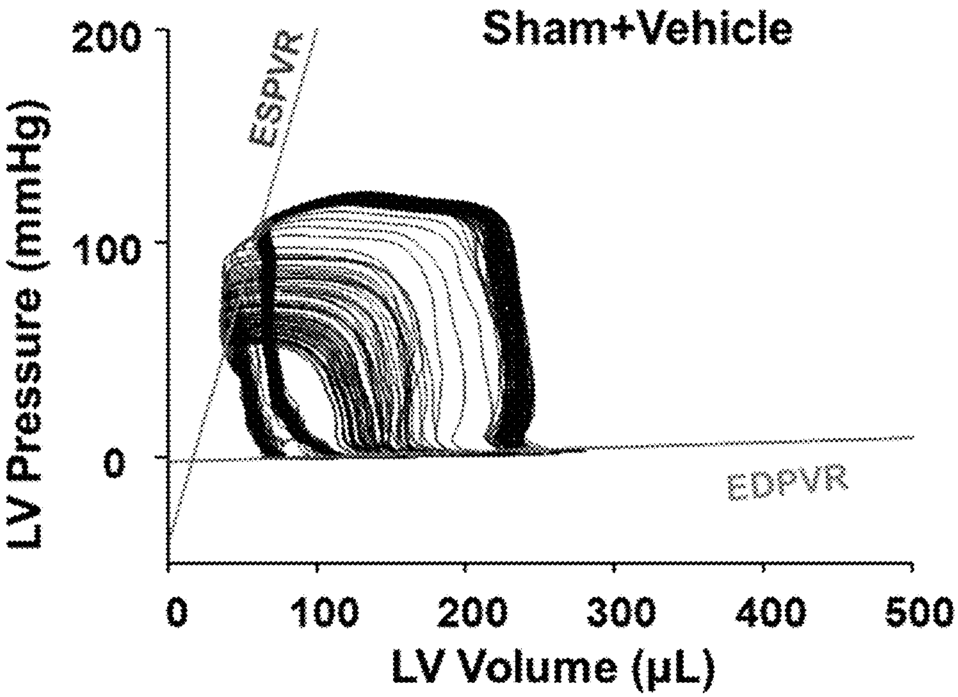
FIG. 5A-F shows original 10-sec recordings of steady state P-V loops obtained with a Millar P-V conductance catheter system from sham+vehicle, sham+RTX, CHF+ vehicle and CHF+RTX rats (A-D).
Figure 5B:
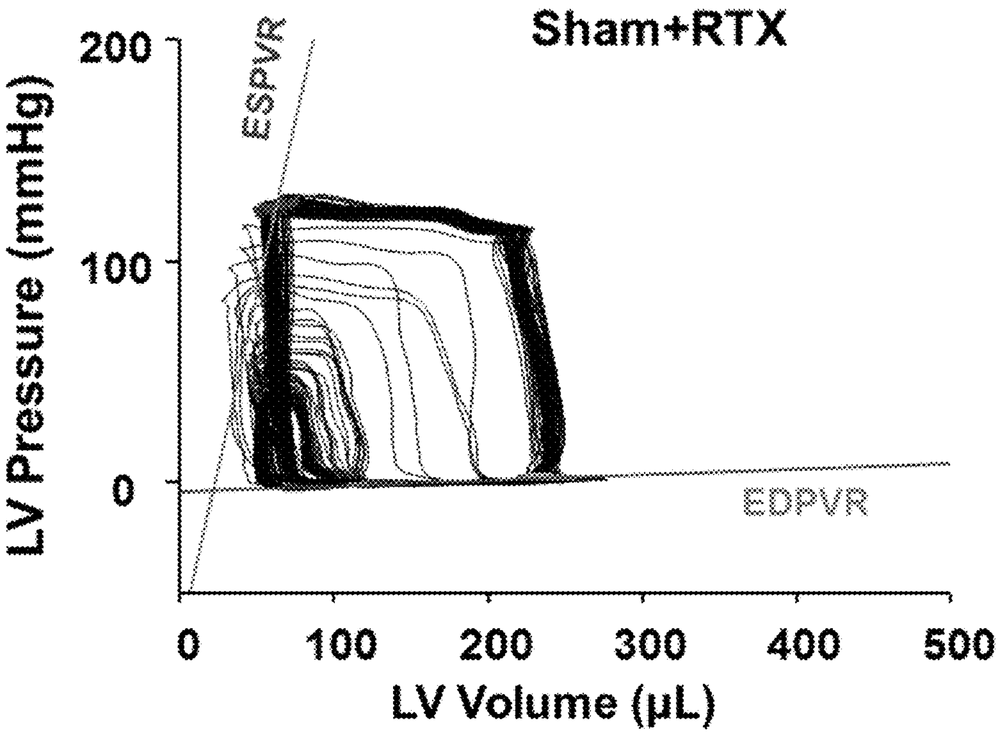
Figure 5C:
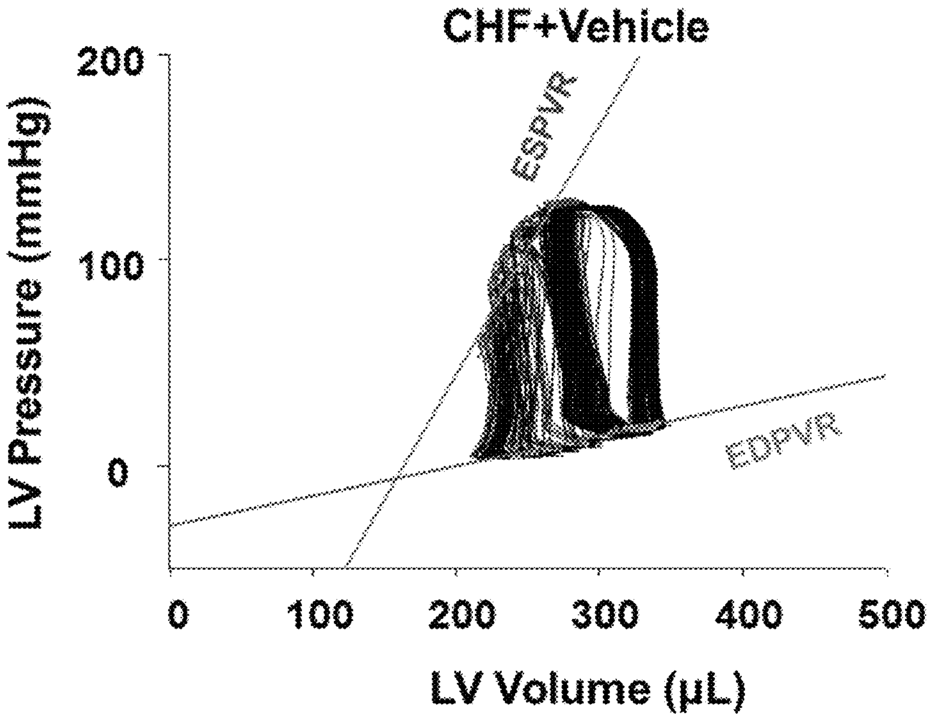
Figure 5D:
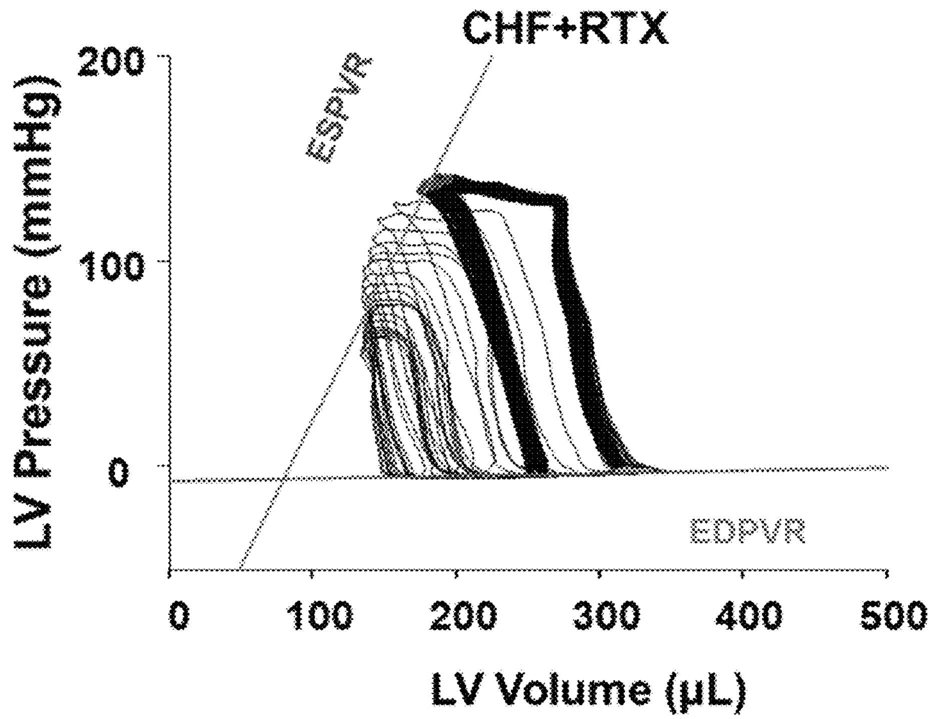
Figure 5E:
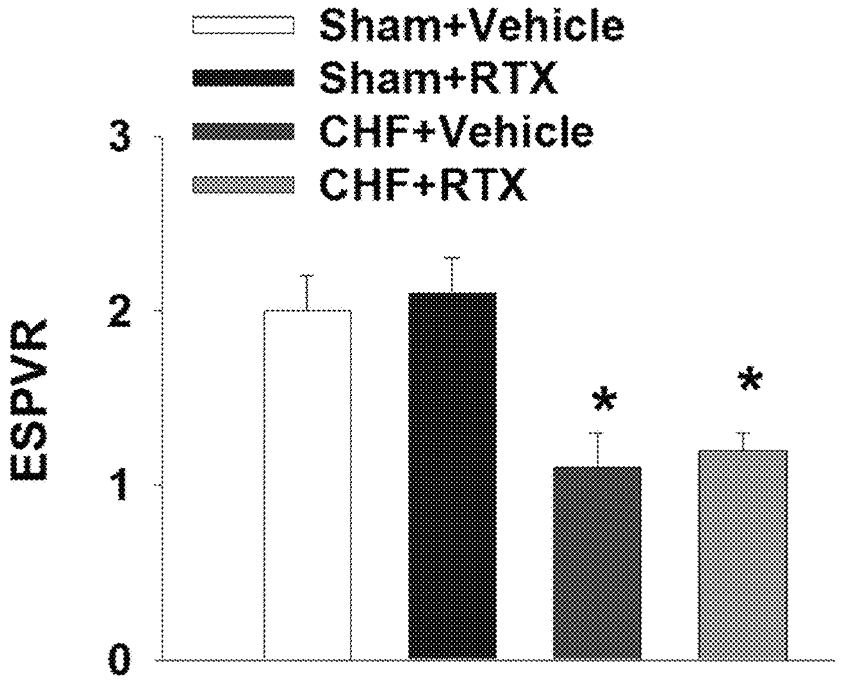
Figure 5F:
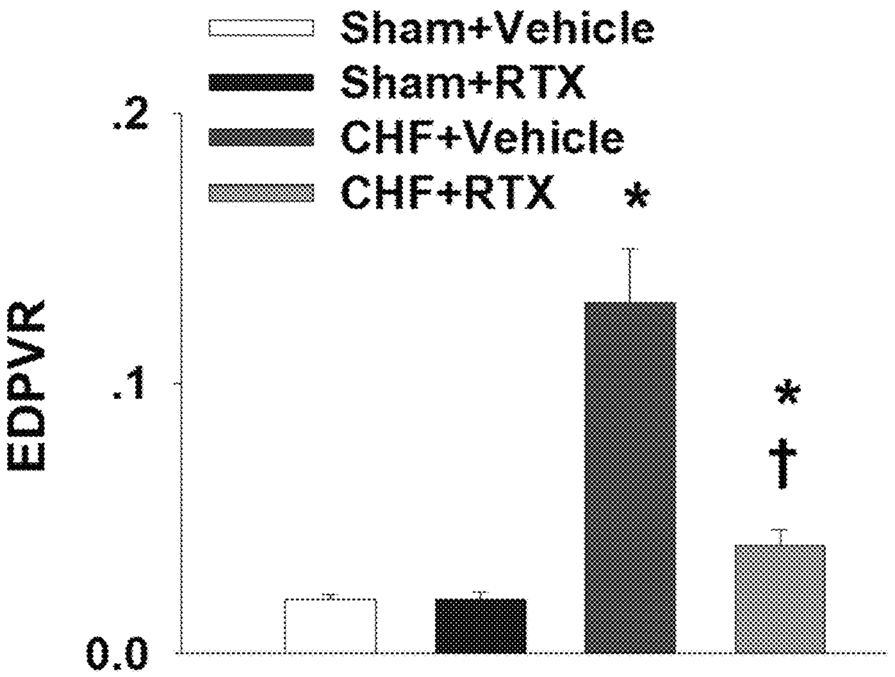

This example illustrates In vivo PV loop analysis in sham and CHF rats treated with vehicle or RTX. Using left ventricular PV loop analysis (FIG. 5A-F), basal load-independent contractile function, as measured by the slope of the PRSW relationship and ESPVR, was significantly reduced in CHF+vehicle rats compared to sham+vehicle rats. Load sensitive measures of systolic and diastolic function such as the maximum and minimum rates of pressure change ($dP/dt_{max}$ and $dP/dt_{min}$) and ejection fraction were also significantly lower in CHF+vehicle compared to sham+vehicle rats. Furthermore, compared to sham+vehicle rats, higher Tau (a measurement of ventricular relaxation) and LVEDP were found in CHF+vehicle rats, indicating compromised LV active and passive diastolic function. In addition, compared to sham+vehicle rats, CHF+vehicle rats presented with significant LV chamber enlargement, as shown by increased end systolic and diastolic volume. These data are consistent with the data obtained by echocardiographic measurements. The end diastolic pressure volume relationship (EDPVR) was also significantly elevated in CHF+vehicle rats compared to sham+vehicle rats, suggesting increased ventricular stiffness in CHF (FIG. 5A-F). Compared to the CHF+vehicle rats, structural and functional abnormalities were ameliorated by RTX, as shown by a reduction in LV chamber size, increased $dP/dt_{min}$, reduced Tau and LVEDP as well as reduced stiffness as shown by the EDPVR (FIG. 5E-F). Interestingly, RTX treatment did not have a significant effect on basal contractile function such as $dP/dt_{max}$, PRSW and ESPVR in CHF rats. In addition, RTX had no effect on contractile and relaxation parameters in sham rats.

Example 7

This example illustrates effects of RTX on cardiac apoptosis in sham and CHF rats.

Figure 6A:
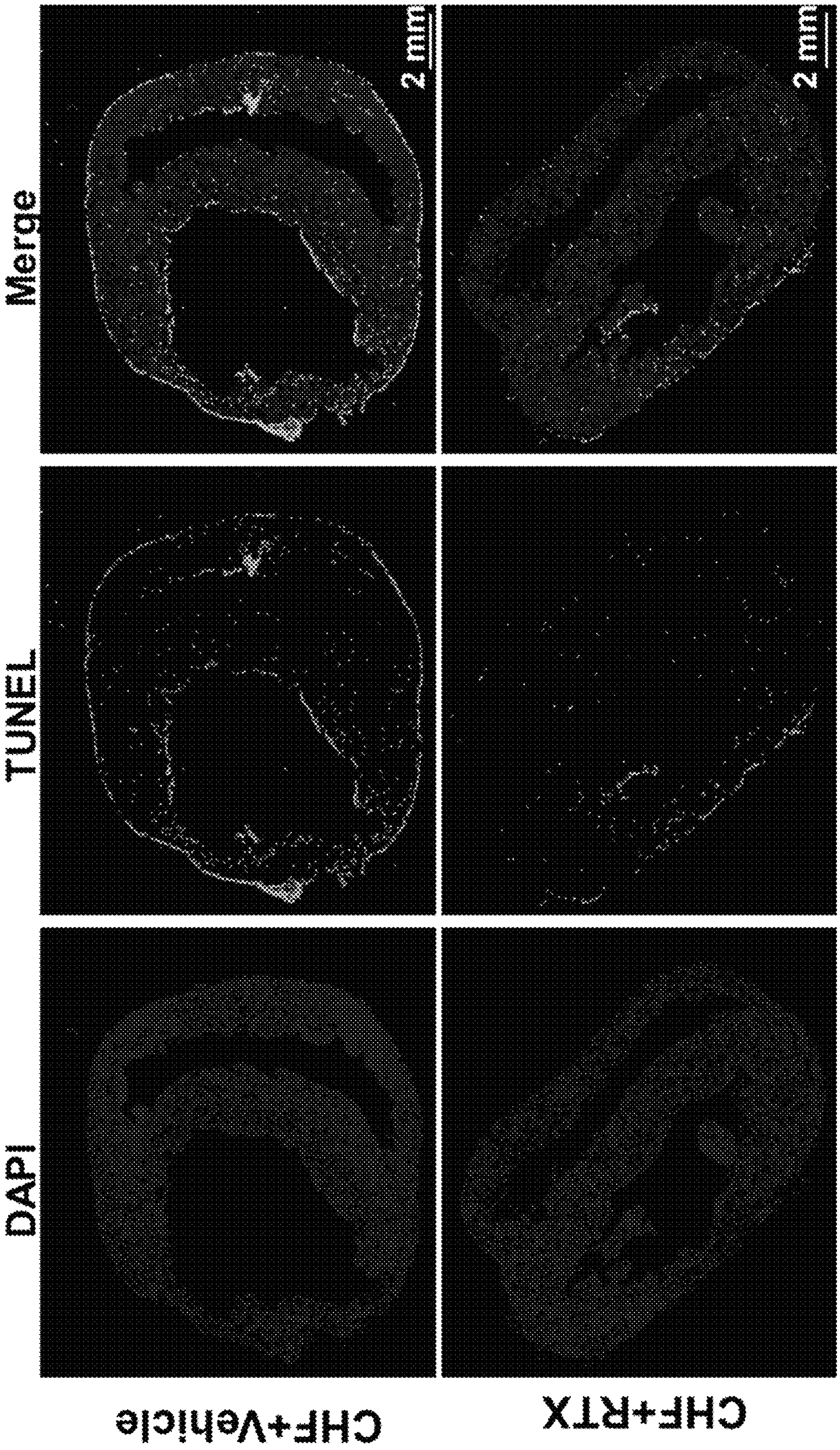
FIG. 6A-E shows representative scanning images (A) and mean data (B-E) showing TUNEL-positive staining in LV infarct, LV pen-infarct, LV remote and IVS regions from sham+vehicle, sham+RTX, CHF+Vehicle and CHF+RTX rats. Data are expressed as mean±SE. n=5-6/each group. *, P<0.05 vs. sham+vehicle, †, P<0.05 vs. CHF+vehicle.
Figure 6B:
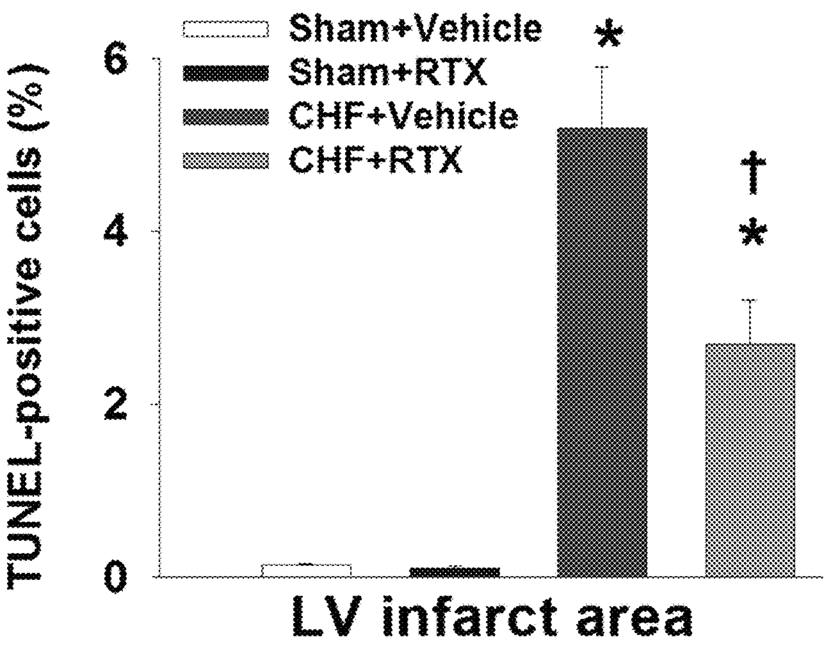
Figure 6C:
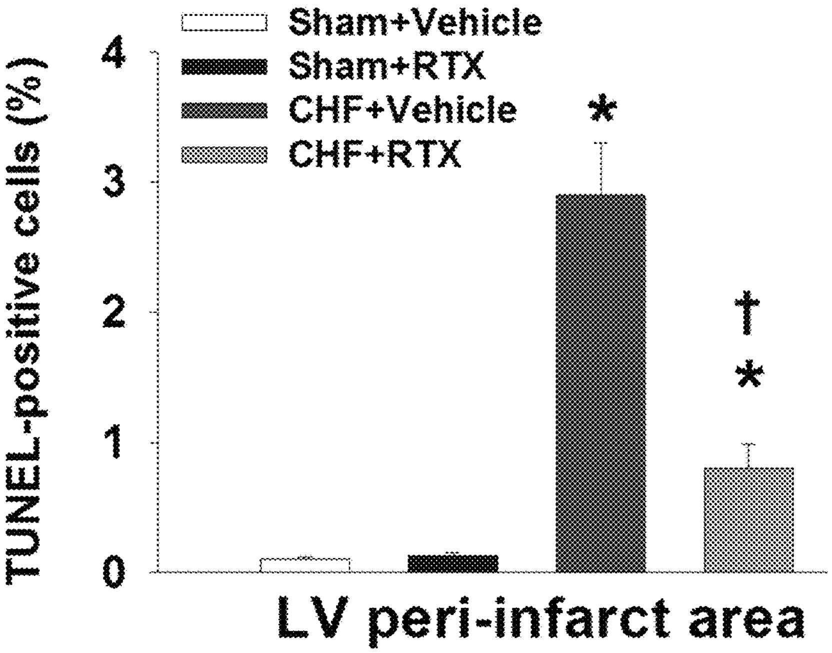
Figure 6D:
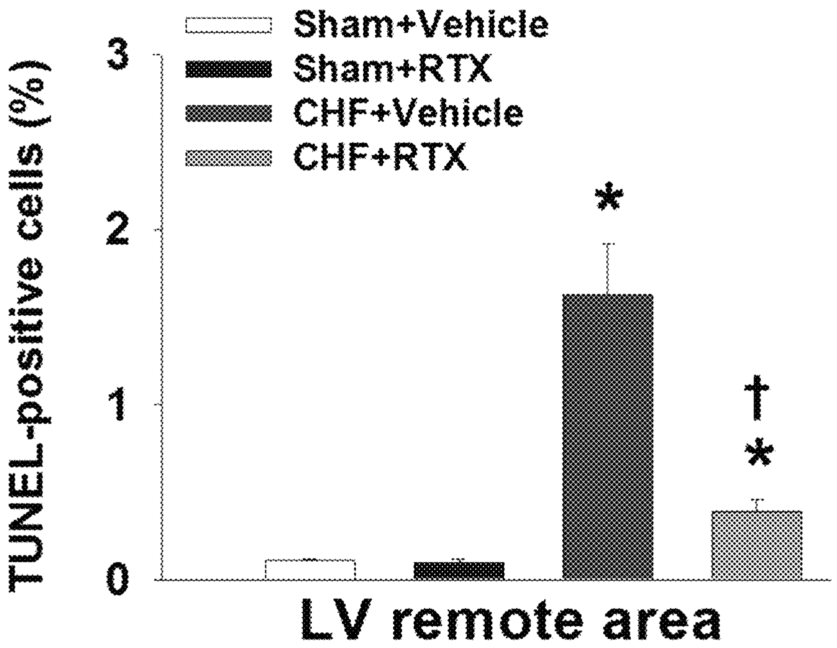
Figure 6E:
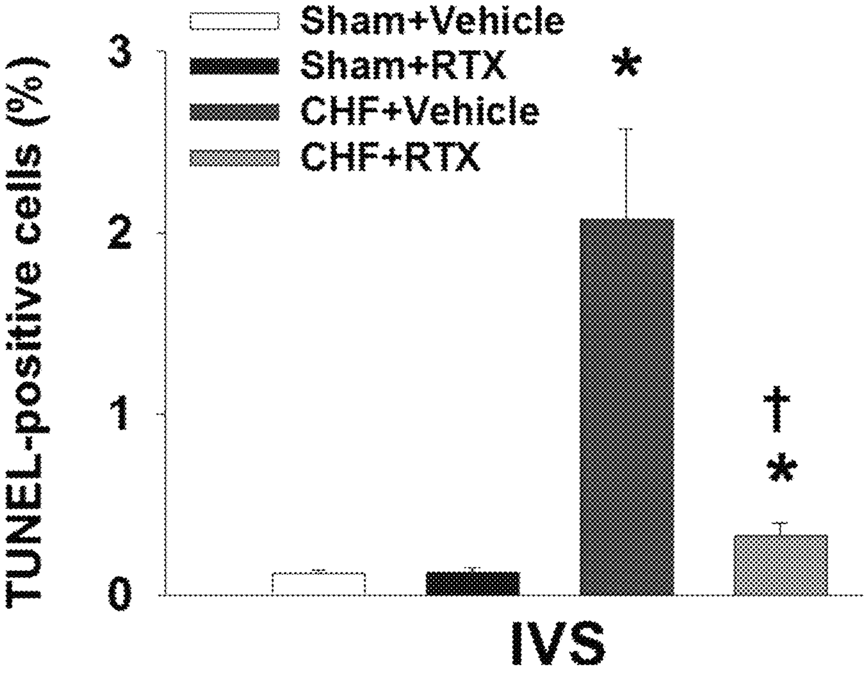

Cardiac remodeling includes hypertrophy, fibrosis and apoptosis. Based on the beneficial effects of RTX on cardiac hypertrophy and cardiac fibrosis in CHF rats, we further investigated the effect of RTX on cardiac apoptosis in sham and CHF rats. TUNEL staining was performed. Terminal deoxynucleotidyl transferase dUTP-mediated nick-end labeling (TUNEL) staining and analysis was performed to evaluate the effect of RTX on cardiac apoptosis. Representative photomicrographs are depicted in FIG. 6A. We found that compared to sham+vehicle rats, there was a significant increase in TUNEL-positive cells in the LV infarct, LV peri-infarct, LV remote and IVS regions of the myocardium in CHF+vehicle rats (FIG. 6B-6E). However, TUNEL-positive cells were markedly reduced in the LV infarct, LV pen-infarct, LV remote and IVS regions of the myocardium from CHF+RTX rats compared to CHF+vehicle rats (FIG. 6B-E). There was no significant difference in the number of TUNEL-positive cells in the heart between sham+vehicle and sham+RTX rats. Furthermore, data from immunohistochemical staining demonstrated that there were increased cleaved caspase 3-positive cardiomyocytes in the LV peri-infarct, LV remote and IVS regions of the myocardium in CHF+vehicle rats compared to sham+vehicle rats, which was largely prevented by epicardial application of RTX following coronary artery ligation. In addition, protein expression of cleaved caspase 3 in LV remote and IVS regions of the myocardium was significantly increased in CHF+vehicle rats compared to sham+vehicle rats whereas RTX treatment prevented the elevated protein expression of cleaved caspase 3 in the myocardium of CHF rats.

Example 8

Figure 7:
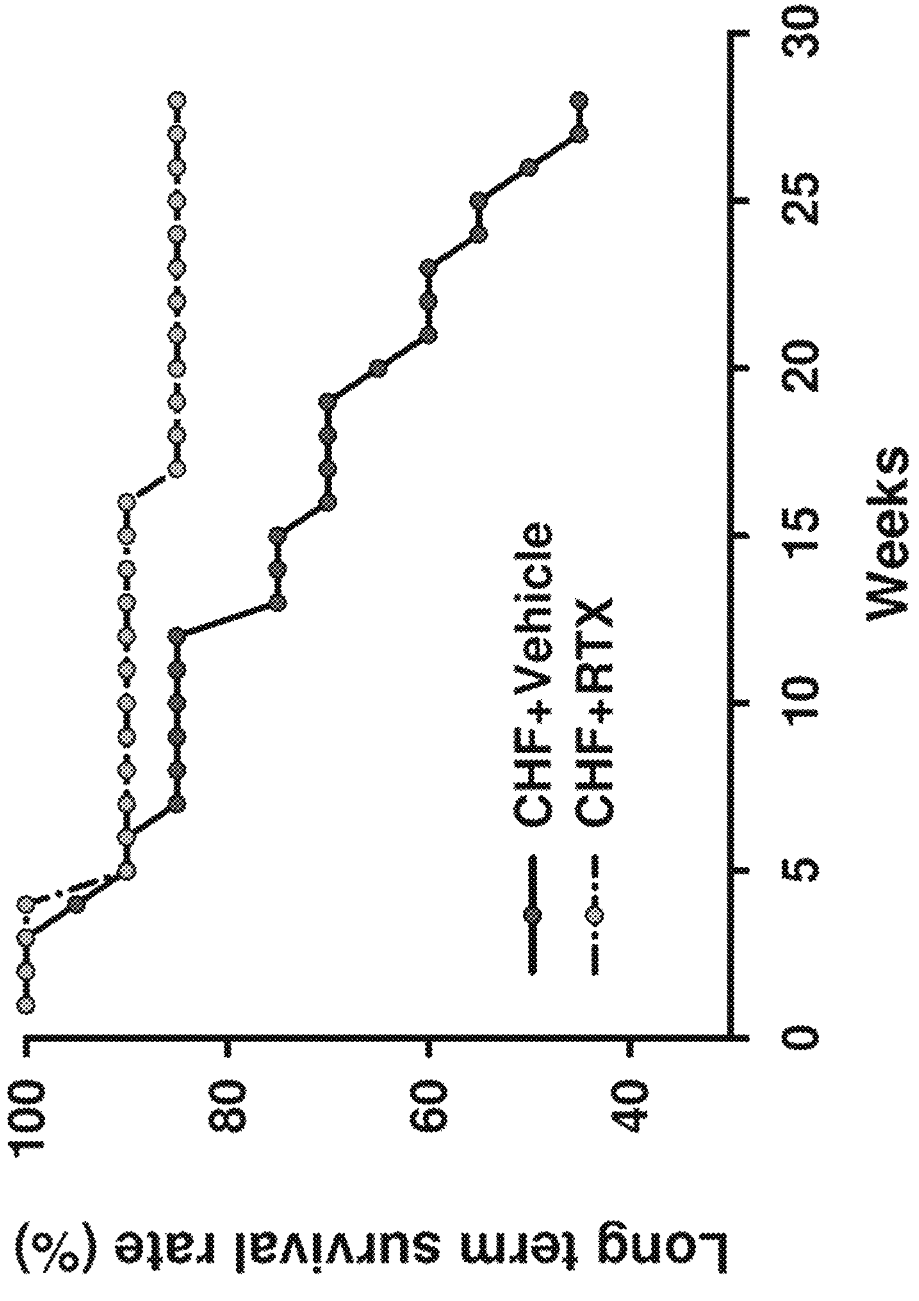
FIG. 7 shows a comparison for long term survival of rats treated with epicardial application of vehicle (saline) or RTX (50 μg/ml, Sigma, catalog No. R8756) after induction a myocardial infarction (MI) by coronary artery ligation.

This example illustrates effects of RTX on the long-term survival rate of post MI rats. In FIG. 7, we provide evidence showing that epicardial application of RTX (50 μg/ml) at the time of coronary ligation markedly improved long-term (6 months) survival rates in CHF rats. Over a 6 month period over 50% of vehicle-treated rats died. This contrasts with under 20% of RTX treated-rats.

Example 9

This example illustrates local anti-inflammatory effects of RTX in the infarcted heart.

Figure 8A:
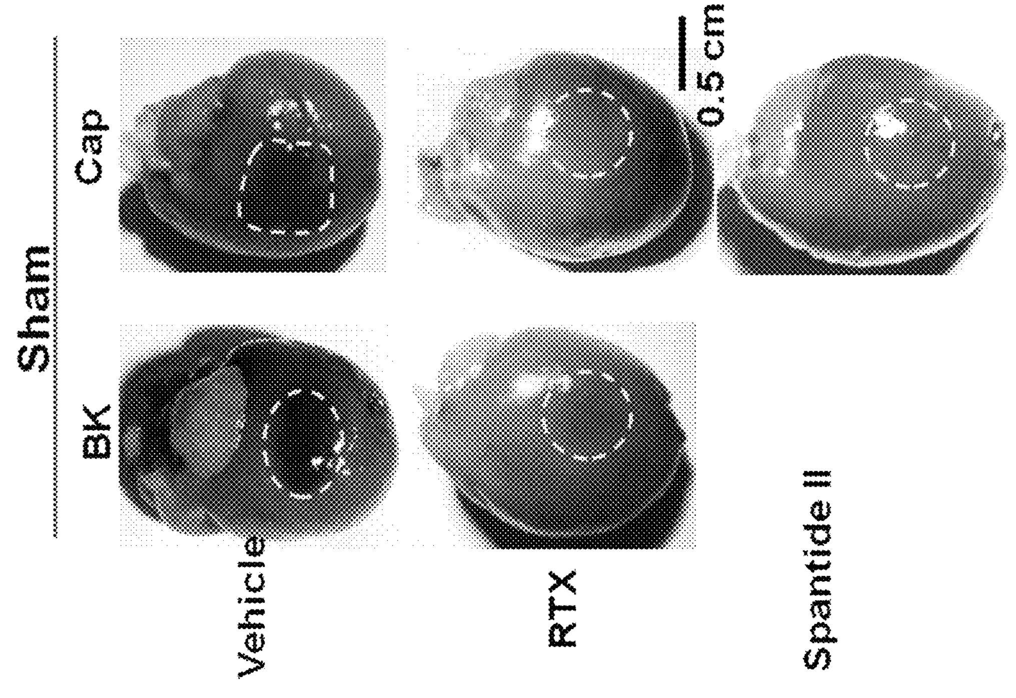
FIG. 8A shows plasma extravasation indicated by the Evans Blue area following CSAR activation following epicardial application of either capsaicin or bradykinin. This can largely be abolished by either acute pretreatment with an NK1 antagonist (Spantide II, i.v., 0.3 mg/kg) or chronic CSAR denervation by RTX.
Figure 8B:
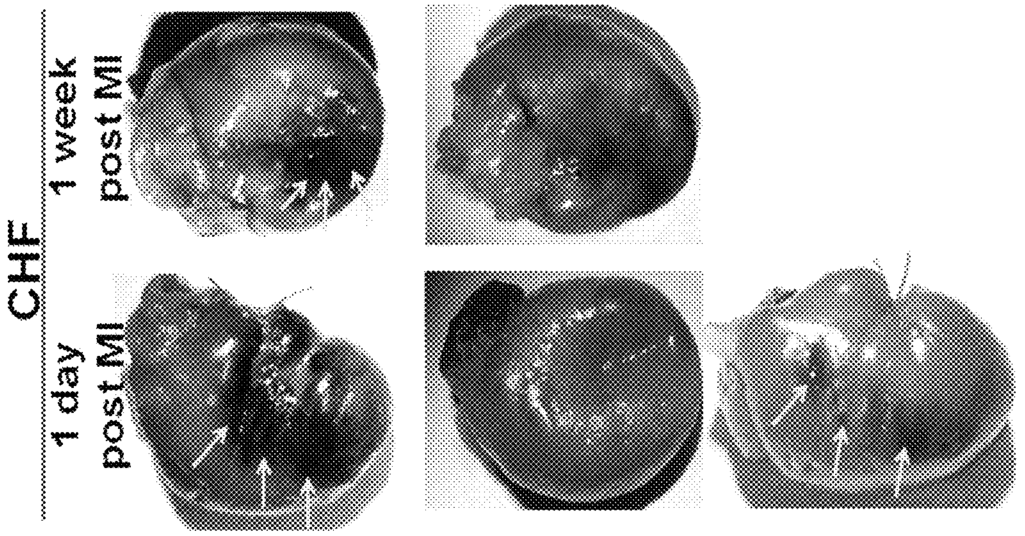
FIG. 8B shows that cardiac plasma extravasation occurs 1 day after MI and lasts more than 1 week. This response can be almost completely abolished by pretreatment with epicardial application of RTX or attenuated by pretreatment with Spantide II (i.v., 0.3 mg/kg, 2 minutes prior to Evans Blue) at the time of coronary ligation.
Figure 8C:
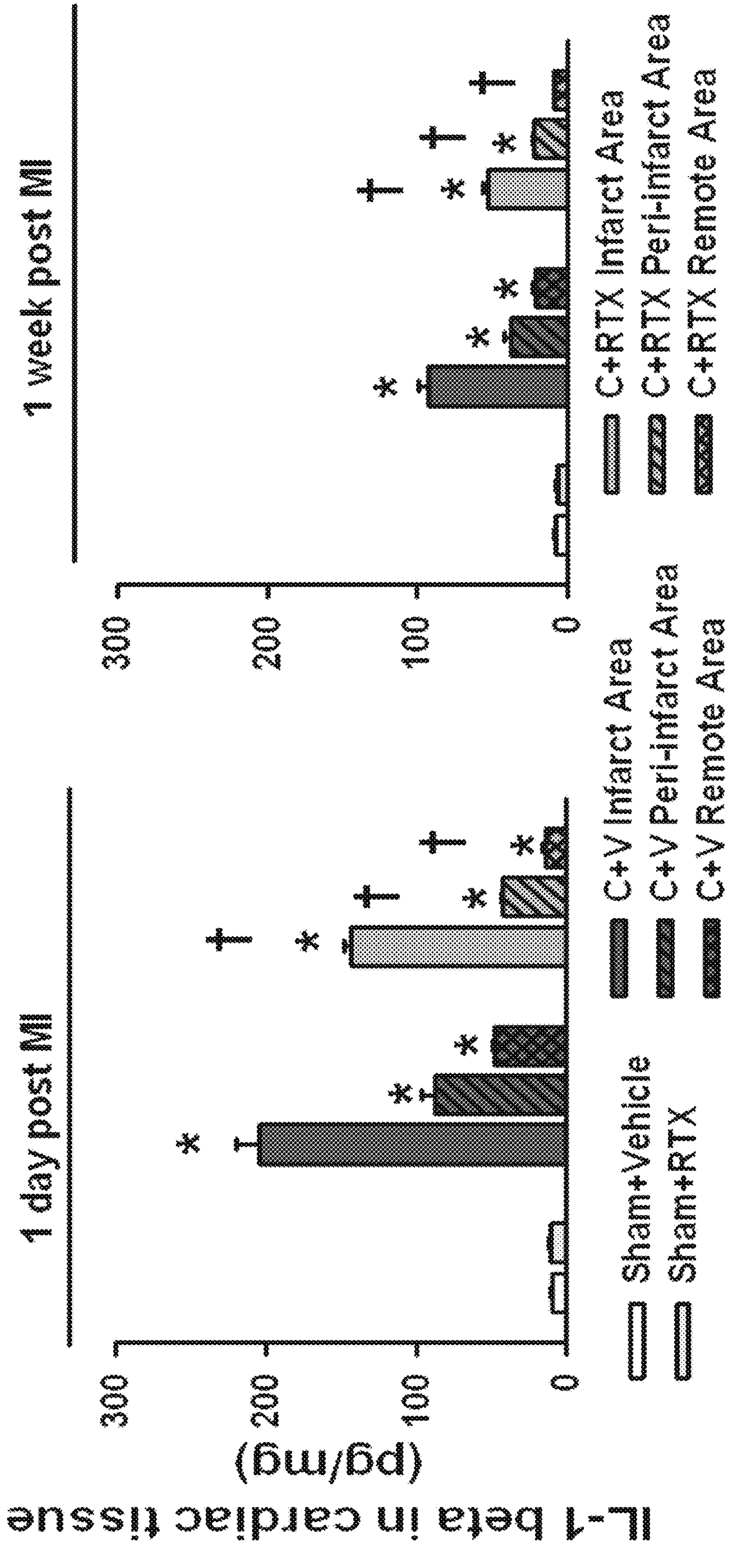
FIG. 8C shows cardiac inflammatory cytokine IL-β3 levels in the infarct, periinfarct and remote areas at 1 day or 1 week after MI in rats treated with epicardial application of vehicle or RTX during MI. n=3/each group. * P<0.05 vs. sham+vehicle, †, P<0.05 vs. CHF (C)+vehicle (V).

Myocardial ischemia causes the production and release of several metabolites including bradykinin, prostaglandins and protons that stimulate cardiac sympathetic afferent nerve endings leading to increases in BP, HR and sympathetic nerve activity. As cardiac TRPV1-expressing sympathetic afferents also subserve a "dual sensory-efferent" function and release pro-inflammatory neuropeptides, we hypothesized that plasma extravasation and cardiac neuroinflammation follows myocardial ischemia. FIG. 8B shows first direct evidence that marked cardiac plasma extravasation (indicated by Evans Blue area) occurs at day 1 after MI and lasts for more than 1 week. This effect was almost completely abolished by pretreatment with epicardial application of RTX at the time of coronary ligation or attenuated by pretreatment with the NK1 antagonist Spantide II (0.3 mg/kg, i.v., 2 min prior to injection of Evans Blue). On the other hand, cardiac inflammatory cytokine (e.g. IL-1 (3) levels in the infarct, peri-infarct and remote areas are significantly increased at day 1 after MI and lasts more than 1 week. The increased IL-1 β expression in pen-infarct and remote areas post MI were markedly attenuated by pretreatment with epicardial application of RTX whereas the increased IL-1 β level in the infarct area was partially prevented by RTX (FIG. 8C). The differential effects of RTX on IL-1 β expression between infarct and non-infarct (pen-infarct and remote) areas may be due to different sources of cardiac inflammation in these areas. Inflammation in the infarct area may be due to tissue death whereas in peri-infarct and remote areas may be due to cardiac sympathetic afferent mediated neuroinflammation. This may explain why RTX prevented cardiac inflammation in non-infarct areas to a greater extent than in the infarct area. These data suggest that RTX imparted a potent anti-inflammatory effect in the infarcted heart through a cardiac sympathetic afferent denervation. Considering that cardiac inflammation is an initial event triggering downstream cascades of cardiac remodeling post MI, these data provide a novel mechanistic explanation for our recent findings namely that CSAR denervation during MI markedly reduces the cardiac remodeling process in CHF.

We claim:

1. A method for administering a formulation comprising resiniferatoxin (RTX) to a patient, the method comprising administering the formulation via catheter-based administration into the coronary artery circulation or pericardiocentesis, wherein the patient has or is at risk of having one or more of: heart failure, cardiac inflammation, or cardiac fibrosis, which are induced by myocardial infarction.

2. The method of claim 1, wherein the formulation is administered as a single dose.

3. The method of claim 1, wherein the formulation is administered over a length of time from about 1 minute to about 5 minutes.

4. The method of claim 1, wherein the formulation is delivered as one or more boluses.

5. The method of claim 1, wherein the concentration of RTX in the formulation is about 100 ng/ml to about 500 μg/ml.

6. The method of claim 1, wherein the concentration of RTX in the formulation is about 5 μg/ml to about 80 μg/ml.

7. The method of claim 1, wherein the concentration of RTX in the formulation is about 20 μg/ml to about 60 μg/ml.

8. The method of claim 1, wherein the patient is an adult human patient.

9. A method for reducing cardiac inflammation induced by myocardial infarction in a patient, comprising administering a formulation comprising resiniferatoxin (RTX) via catheter-based administration into the coronary artery circulation or pericardiocentesis.

10. The method of claim 9, wherein the concentration of RTX in the formulation is about 100 ng/ml to about 500 μg/ml.

11. The method of claim 9, wherein the concentration of RTX in the formulation is about 5 μg/ml to about 80 μg/ml.

12. The method of claim 9, wherein the concentration of RTX in the formulation is about 20 μg/ml to about 60 μg/ml.

13. A method for treating heart failure induced by myocardial infarction or a myocardial infarction-related condition in a patient, comprising administering a formulation comprising resiniferatoxin (RTX) via catheter-based administration into the coronary artery circulation or pericardiocentesis; wherein the related condition is increased sympatho-excitation, cardiac hypertrophy, increased left ventricular end diastolic pressure (LVEDP), lung edema, or a combination thereof.

14. The method of claim 13, wherein the concentration of RTX in the formulation is about 100 ng/ml to about 500 μg/ml.

15. The method of claim 13, wherein the concentration of RTX in the formulation is about 5 μg/ml to about 80 μg/ml.

16. The method of claim 13, wherein the concentration of RTX in the formulation is about 20 μg/ml to about 60 μg/ml.

17. The method of claim 1, wherein a cardiac sympathetic afferent reflex (CSAR) is attenuated for a period of at least one week after the administration.

18. The method of claim 17, wherein the CSAR is attenuated for a period of four weeks after the administration.

19. The method of claim 9, wherein a cardiac sympathetic afferent reflex (CSAR) is attenuated for a period of at least one week after the administration.

20. The method of claim 19, wherein the CSAR is attenuated for a period of four weeks after the administration.

21. The method of claim 13, wherein a cardiac sympathetic afferent reflex (CSAR) is attenuated for a period of at least one week after the administration.

22. The method of claim 21, wherein the CSAR is attenuated for a period of four weeks after the administration.

* * * * *